United States Patent
Clark et al.

(10) Patent No.: US 11,548,935 B2
(45) Date of Patent: Jan. 10, 2023

(54) PEPTIDES DERIVED FROM FIBRONECTIN WITH IMPROVED BIOACTIVITY AND REDUCED SUSCEPTIBILITY TO NEUTROPHIL ELASTASE DEGRADATION

(71) Applicant: NeoMatrix Therapeutics Inc., Stony Brook, NY (US)

(72) Inventors: Richard August Clark, Setauket, NY (US); Fubao Lin, Stony Brook, NY (US)

(73) Assignee: NeoMatrix Therapeutics Inc., Stony Brook, NY (US)

( * ) Notice: Subject to any disclaimer, the term of this patent is extended or adjusted under 35 U.S.C. 154(b) by 350 days.

(21) Appl. No.: 16/341,686

(22) PCT Filed: Oct. 12, 2017

(86) PCT No.: PCT/US2017/056399
§ 371 (c)(1),
(2) Date: Apr. 12, 2019

(87) PCT Pub. No.: WO2018/071709
PCT Pub. Date: Apr. 19, 2018

(65) Prior Publication Data
US 2020/0223903 A1 Jul. 16, 2020

Related U.S. Application Data

(60) Provisional application No. 62/408,222, filed on Oct. 14, 2016.

(51) Int. Cl.
*C07K 14/78* (2006.01)
*A61P 17/02* (2006.01)
*A61K 38/00* (2006.01)
*C07K 5/12* (2006.01)
*C07K 7/50* (2006.01)

(52) U.S. Cl.
CPC .............. *C07K 14/78* (2013.01); *A61P 17/02* (2018.01); *A61K 38/00* (2013.01); *C07K 5/12* (2013.01); *C07K 7/50* (2013.01)

(58) Field of Classification Search
CPC ...... A61K 38/39; A61K 9/0014; A61K 35/36; A61K 35/16; A61K 38/18; A61K 8/64; A61K 47/42; A61P 17/02; A61P 35/00; A61L 27/54; A61L 2300/414; A61L 27/24; A61Q 19/00; A61Q 19/08; C07K 14/705; C07K 14/61; A61F 2310/00365
See application file for complete search history.

(56) References Cited

U.S. PATENT DOCUMENTS

2010/0292161 A1* 11/2010 Clark .................... A61L 27/227
514/19.3

FOREIGN PATENT DOCUMENTS

| WO | 2002090377 | 11/2002 |
| WO | 2005117936 | 12/2005 |
| WO | 2007044396 | 4/2007 |

OTHER PUBLICATIONS

Ashrafi et al. "Novel Formation of Common Wound Bacterial Biofilms on Human Incisional and Excisional Cutaneous Wound Models Enables Identification of Bacterial-Specific Volatile Organic Compound Profiles With Clinical Translatability in Wound Infection Theranostics" Abstract from the 29th Annual Meeting of the Wound Healing Society, SAWC-Spring/WHS Joint Meeting, Wound Repair and Regeneration, p. A1 (2017).
Clark et al. "Reengineering a Fibronectin-Derived Peptide for Topical Treatment of Burns and Chronic Wounds" Abstract from the 29th Annual Meeting of the Wound Healing Society, SAWC-Spring/WHS Joint Meeting, Wound Repair and Regeneration, pp. A6-A7 (2017).
Extended European Search Report correspondence to European Patent Application No. 17859564.1 (7 pages) (dated Feb. 19, 2020).
International Preliminary Report on Patentability corresponding to International Patent Application No. PCT/US2017/056399 (7 pages) (dated Apr. 16, 2019).
International Search Report and the Written Opinion of the International Searching Authority corresponding to International Patent Application No. PCT/US2017/056399 (10 pages) (dated Jan. 24, 2018).
Lin et al. "Fibronectin Growth Factor-Binding Domains Are Required for Fibroblast Survival" Journal of Investigative Dermatology, 131:84-98 (2011).
Lin et al. "Fibronectin peptides that bind PDGF-BB enhance survival of cells and tissue under stress" Journal of Investigative Dermatology, 134(4):1119-1127 (2014).
Sottile et al. "Fibronectin Polymerization Regulates the Composition and Stability of Extracellular Matrix Fibrils and Cell-Matrix Adhesions" Molecular Biology of the Cell, 13:3546-3559 (2002).

\* cited by examiner

*Primary Examiner* — Aradhana Sasan
*Assistant Examiner* — Jia-Hai Lee
(74) *Attorney, Agent, or Firm* — Myers Bigel, P.A.

(57) ABSTRACT

Polypeptides derived from fibronectin are presented that are neutrophil elastase-resistant and can bind to growth factors and/or enhance growth factor activity. These polypeptides are useful for enhancing wound healing in a patient.

13 Claims, 11 Drawing Sheets

Specification includes a Sequence Listing.

```
                        SEQUENCE LISTING

<160> NUMBER OF SEQ ID NOS: 112

<210> SEQ ID NO 1
<211> LENGTH: 15
<212> TYPE: PRT
<213> ORGANISM: Artificial Sequence
<220> FEATURE:
<223> OTHER INFORMATION: polypeptide according to formula I
<220> FEATURE:
<221> NAME/KEY: MISC_FEATURE
<222> LOCATION: (2)..(2)
<223> OTHER INFORMATION: is I or G or L
<220> FEATURE:
<221> NAME/KEY: MISC_FEATURE
<222> LOCATION: (3)..(3)
<223> OTHER INFORMATION: is S or G
<220> FEATURE:
<221> NAME/KEY: MISC_FEATURE
<222> LOCATION: (6)..(6)
<223> OTHER INFORMATION: is I or G or L
<220> FEATURE:
<221> NAME/KEY: MISC_FEATURE
<222> LOCATION: (7)..(7)
<223> OTHER INFORMATION: is L or G
<220> FEATURE:
<221> NAME/KEY: MISC_FEATURE
<222> LOCATION: (13)..(13)
<223> OTHER INFORMATION: is N or G
<220> FEATURE:
<221> NAME/KEY: MISC_FEATURE
<222> LOCATION: (14)..(14)
<223> OTHER INFORMATION: is absent or S
<220> FEATURE:
<221> NAME/KEY: MISC_FEATURE
<222> LOCATION: (15)..(15)
<223> OTHER INFORMATION: is absent or V

<400> SEQUENCE: 1

His Xaa Xaa Lys Tyr Xaa Xaa Arg Trp Arg Pro Lys Xaa Xaa Xaa
1               5                   10                  15

<210> SEQ ID NO 2
<211> LENGTH: 14
<212> TYPE: PRT
<213> ORGANISM: Artificial Sequence
<220> FEATURE:
<223> OTHER INFORMATION: polypeptide according to formula I
<220> FEATURE:
<221> NAME/KEY: MISC_FEATURE
<222> LOCATION: (2)..(2)
<223> OTHER INFORMATION: is I or G or L
<220> FEATURE:
<221> NAME/KEY: MISC_FEATURE
<222> LOCATION: (3)..(3)
<223> OTHER INFORMATION: is S or G
<220> FEATURE:
<221> NAME/KEY: MISC_FEATURE
<222> LOCATION: (6)..(6)
<223> OTHER INFORMATION: is I or G or L
<220> FEATURE:
<221> NAME/KEY: MISC_FEATURE
<222> LOCATION: (7)..(7)
<223> OTHER INFORMATION: is L or G
<220> FEATURE:
<221> NAME/KEY: MISC_FEATURE
<222> LOCATION: (13)..(13)
<223> OTHER INFORMATION: is N or G
<220> FEATURE:
<221> NAME/KEY: MISC_FEATURE
```

<222> LOCATION: (14)..(14)
<223> OTHER INFORMATION: is absent or S

<400> SEQUENCE: 2

His Xaa Xaa Lys Tyr Xaa Xaa Arg Trp Arg Pro Lys Xaa Xaa
1               5                   10

<210> SEQ ID NO 3
<211> LENGTH: 13
<212> TYPE: PRT
<213> ORGANISM: Artificial Sequence
<220> FEATURE:
<223> OTHER INFORMATION: polypeptide according to formula I
<220> FEATURE:
<221> NAME/KEY: MISC_FEATURE
<222> LOCATION: (2)..(2)
<223> OTHER INFORMATION: is I or G or L
<220> FEATURE:
<221> NAME/KEY: MISC_FEATURE
<222> LOCATION: (3)..(3)
<223> OTHER INFORMATION: is S or G
<220> FEATURE:
<221> NAME/KEY: MISC_FEATURE
<222> LOCATION: (6)..(6)
<223> OTHER INFORMATION: is I or G or L
<220> FEATURE:
<221> NAME/KEY: MISC_FEATURE
<222> LOCATION: (7)..(7)
<223> OTHER INFORMATION: is L or G
<220> FEATURE:
<221> NAME/KEY: MISC_FEATURE
<222> LOCATION: (13)..(13)
<223> OTHER INFORMATION: is N or G

<400> SEQUENCE: 3

His Xaa Xaa Lys Tyr Xaa Xaa Arg Trp Arg Pro Lys Xaa
1               5                   10

<210> SEQ ID NO 4
<211> LENGTH: 14
<212> TYPE: PRT
<213> ORGANISM: Artificial Sequence
<220> FEATURE:
<223> OTHER INFORMATION: polypeptide according to formula I
<220> FEATURE:
<221> NAME/KEY: MISC_FEATURE
<222> LOCATION: (2)..(2)
<223> OTHER INFORMATION: is I or G or L
<220> FEATURE:
<221> NAME/KEY: MISC_FEATURE
<222> LOCATION: (3)..(3)
<223> OTHER INFORMATION: is S or G
<220> FEATURE:
<221> NAME/KEY: MISC_FEATURE
<222> LOCATION: (6)..(6)
<223> OTHER INFORMATION: is I or G or L
<220> FEATURE:
<221> NAME/KEY: MISC_FEATURE
<222> LOCATION: (7)..(7)
<223> OTHER INFORMATION: is L or G
<220> FEATURE:
<221> NAME/KEY: MISC_FEATURE
<222> LOCATION: (13)..(13)
<223> OTHER INFORMATION: is N or G
<220> FEATURE:
<221> NAME/KEY: MISC_FEATURE
<222> LOCATION: (14)..(14)
<223> OTHER INFORMATION: is absent or V

<400> SEQUENCE: 4

His Xaa Xaa Lys Tyr Xaa Xaa Arg Trp Arg Pro Lys Xaa Xaa
1               5                   10

```
<210> SEQ ID NO 5
<211> LENGTH: 13
<212> TYPE: PRT
<213> ORGANISM: Artificial Sequence
<220> FEATURE:
<223> OTHER INFORMATION: P45 peptide

<400> SEQUENCE: 5

Ser Lys Tyr Ile Leu Arg Trp Arg Pro Lys Asn Ser Val
1               5                   10

<210> SEQ ID NO 6
<211> LENGTH: 15
<212> TYPE: PRT
<213> ORGANISM: Artificial Sequence
<220> FEATURE:
<223> OTHER INFORMATION: NP9 peptide

<400> SEQUENCE: 6

His Ile Ser Lys Tyr Ile Leu Gly Trp Arg Pro Lys Asn Ser Val
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: NP10 peptide

<400> SEQUENCE: 7

His Ile Ser Lys Tyr Ile Leu Arg Gly Arg Pro Lys Asn Ser Val
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: NP11 peptide

<400> SEQUENCE: 8

His Ile Ser Lys Tyr Ile Leu Arg Trp Gly Pro Lys Asn Ser Val
1               5                   10                  15

<210> SEQ ID NO 9
<211> LENGTH: 13
<212> TYPE: PRT
<213> ORGANISM: Artificial Sequence
<220> FEATURE:
<223> OTHER INFORMATION: polypeptide according to formula I

<400> SEQUENCE: 9

His Ile Ser Lys Tyr Ile Leu Arg Trp Arg Pro Lys Asn
1               5                   10

<210> SEQ ID NO 10
<211> LENGTH: 15
<212> TYPE: PRT
<213> ORGANISM: Artificial Sequence
<220> FEATURE:
<223> OTHER INFORMATION: polypeptide according to formula I

<400> SEQUENCE: 10

His Ile Ser Lys Tyr Ile Leu Arg Trp Arg Pro Lys Asn Ser Val
1               5                   10                  15

<210> SEQ ID NO 11
```

```
<211> LENGTH: 15
<212> TYPE: PRT
<213> ORGANISM: Artificial Sequence
<220> FEATURE:
<223> OTHER INFORMATION: polypeptide according to formula I

<400> SEQUENCE: 11

His Ile Gly Lys Tyr Gly Leu Arg Trp Arg Pro Lys Asn Ser Val
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: polypeptide according to formula I

<400> SEQUENCE: 12

His Ile Gly Lys Tyr Gly Leu Arg Trp Arg Pro Lys Gly Ser Val
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: polypeptide according to formula I

<400> SEQUENCE: 13

His Gly Ser Lys Tyr Gly Leu Arg Trp Arg Pro Lys Asn Ser Val
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: polypeptide according to formula I

<400> SEQUENCE: 14

His Ile Gly Lys Tyr Ile Gly Arg Trp Arg Pro Lys Asn Ser Val
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: polypeptide according to formula I

<400> SEQUENCE: 15

His Gly Ser Lys Tyr Ile Gly Arg Trp Arg Pro Lys Asn Ser Val
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: polypeptide according to formula I

<400> SEQUENCE: 16

His Gly Ser Lys Tyr Ile Gly Arg Trp Arg Pro Lys Gly Ser Val
1               5                   10                  15

<210> SEQ ID NO 17
<211> LENGTH: 14
```

<212> TYPE: PRT
<213> ORGANISM: Artificial Sequence
<220> FEATURE:
<223> OTHER INFORMATION: polypeptide

<400> SEQUENCE: 17

His Ile Ser Lys Tyr Ile Leu Arg Trp Arg Pro Lys Asn Ser
1               5                   10

<210> SEQ ID NO 18
<211> LENGTH: 15
<212> TYPE: PRT
<213> ORGANISM: Artificial Sequence
<220> FEATURE:
<223> OTHER INFORMATION: polypeptide

<400> SEQUENCE: 18

His Ile Ser Lys Tyr Ile Leu Arg Trp Arg Pro Lys Gly Ser Val
1               5                   10                  15

<210> SEQ ID NO 19
<211> LENGTH: 14
<212> TYPE: PRT
<213> ORGANISM: Artificial Sequence
<220> FEATURE:
<223> OTHER INFORMATION: polypeptide

<400> SEQUENCE: 19

His Ile Ser Lys Tyr Ile Leu Arg Trp Arg Pro Lys Gly Ser
1               5                   10

<210> SEQ ID NO 20
<211> LENGTH: 13
<212> TYPE: PRT
<213> ORGANISM: Artificial Sequence
<220> FEATURE:
<223> OTHER INFORMATION: polypeptide

<400> SEQUENCE: 20

His Ile Ser Lys Tyr Ile Leu Arg Trp Arg Pro Lys Gly
1               5                   10

<210> SEQ ID NO 21
<211> LENGTH: 15
<212> TYPE: PRT
<213> ORGANISM: Artificial Sequence
<220> FEATURE:
<223> OTHER INFORMATION: polypeptide

<400> SEQUENCE: 21

His Gly Ser Lys Tyr Ile Leu Arg Trp Arg Pro Lys Asn Ser Val
1               5                   10                  15

<210> SEQ ID NO 22
<211> LENGTH: 14
<212> TYPE: PRT
<213> ORGANISM: Artificial Sequence
<220> FEATURE:
<223> OTHER INFORMATION: polypeptide

<400> SEQUENCE: 22

His Gly Ser Lys Tyr Ile Leu Arg Trp Arg Pro Lys Asn Ser
1               5                   10

<210> SEQ ID NO 23
<211> LENGTH: 13
<212> TYPE: PRT

```
<213> ORGANISM: Artificial Sequence
<220> FEATURE:
<223> OTHER INFORMATION: polypeptide

<400> SEQUENCE: 23

His Gly Ser Lys Tyr Ile Leu Arg Trp Arg Pro Lys Asn
1               5                   10

<210> SEQ ID NO 24
<211> LENGTH: 15
<212> TYPE: PRT
<213> ORGANISM: Artificial Sequence
<220> FEATURE:
<223> OTHER INFORMATION: polypeptide

<400> SEQUENCE: 24

His Gly Ser Lys Tyr Ile Leu Arg Trp Arg Pro Lys Gly Ser Val
1               5                   10                  15

<210> SEQ ID NO 25
<211> LENGTH: 14
<212> TYPE: PRT
<213> ORGANISM: Artificial Sequence
<220> FEATURE:
<223> OTHER INFORMATION: polypeptide

<400> SEQUENCE: 25

His Gly Ser Lys Tyr Ile Leu Arg Trp Arg Pro Lys Gly Ser
1               5                   10

<210> SEQ ID NO 26
<211> LENGTH: 13
<212> TYPE: PRT
<213> ORGANISM: Artificial Sequence
<220> FEATURE:
<223> OTHER INFORMATION: polypeptide

<400> SEQUENCE: 26

His Gly Ser Lys Tyr Ile Leu Arg Trp Arg Pro Lys Gly
1               5                   10

<210> SEQ ID NO 27
<211> LENGTH: 15
<212> TYPE: PRT
<213> ORGANISM: Artificial Sequence
<220> FEATURE:
<223> OTHER INFORMATION: polypeptide

<400> SEQUENCE: 27

His Leu Ser Lys Tyr Ile Leu Arg Trp Arg Pro Lys Asn Ser Val
1               5                   10                  15

<210> SEQ ID NO 28
<211> LENGTH: 14
<212> TYPE: PRT
<213> ORGANISM: Artificial Sequence
<220> FEATURE:
<223> OTHER INFORMATION: polypeptide

<400> SEQUENCE: 28

His Leu Ser Lys Tyr Ile Leu Arg Trp Arg Pro Lys Asn Ser
1               5                   10

<210> SEQ ID NO 29
<211> LENGTH: 13
<212> TYPE: PRT
<213> ORGANISM: Artificial Sequence
```

```
<220> FEATURE:
<223> OTHER INFORMATION: polypeptide

<400> SEQUENCE: 29

His Leu Ser Lys Tyr Ile Leu Arg Trp Arg Pro Lys Asn
1               5                   10

<210> SEQ ID NO 30
<211> LENGTH: 15
<212> TYPE: PRT
<213> ORGANISM: Artificial Sequence
<220> FEATURE:
<223> OTHER INFORMATION: polypeptide

<400> SEQUENCE: 30

His Leu Ser Lys Tyr Ile Leu Arg Trp Arg Pro Lys Gly Ser Val
1               5                   10                  15

<210> SEQ ID NO 31
<211> LENGTH: 14
<212> TYPE: PRT
<213> ORGANISM: Artificial Sequence
<220> FEATURE:
<223> OTHER INFORMATION: polypeptide

<400> SEQUENCE: 31

His Leu Ser Lys Tyr Ile Leu Arg Trp Arg Pro Lys Gly Ser
1               5                   10

<210> SEQ ID NO 32
<211> LENGTH: 13
<212> TYPE: PRT
<213> ORGANISM: Artificial Sequence
<220> FEATURE:
<223> OTHER INFORMATION: polypeptide

<400> SEQUENCE: 32

His Leu Ser Lys Tyr Ile Leu Arg Trp Arg Pro Lys Gly
1               5                   10

<210> SEQ ID NO 33
<211> LENGTH: 15
<212> TYPE: PRT
<213> ORGANISM: Artificial Sequence
<220> FEATURE:
<223> OTHER INFORMATION: polypeptide

<400> SEQUENCE: 33

His Ile Gly Lys Tyr Ile Leu Arg Trp Arg Pro Lys Asn Ser Val
1               5                   10                  15

<210> SEQ ID NO 34
<211> LENGTH: 14
<212> TYPE: PRT
<213> ORGANISM: Artificial Sequence
<220> FEATURE:
<223> OTHER INFORMATION: polypeptide

<400> SEQUENCE: 34

His Ile Gly Lys Tyr Ile Leu Arg Trp Arg Pro Lys Asn Ser
1               5                   10

<210> SEQ ID NO 35
<211> LENGTH: 13
<212> TYPE: PRT
<213> ORGANISM: Artificial Sequence
<220> FEATURE:
```

```
<223> OTHER INFORMATION: polypeptide

<400> SEQUENCE: 35

His Ile Gly Lys Tyr Ile Leu Arg Trp Arg Pro Lys Asn
1               5                   10

<210> SEQ ID NO 36
<211> LENGTH: 15
<212> TYPE: PRT
<213> ORGANISM: Artificial Sequence
<220> FEATURE:
<223> OTHER INFORMATION: polypeptide

<400> SEQUENCE: 36

His Ile Gly Lys Tyr Ile Leu Arg Trp Arg Pro Lys Gly Ser Val
1               5                   10                  15

<210> SEQ ID NO 37
<211> LENGTH: 14
<212> TYPE: PRT
<213> ORGANISM: Artificial Sequence
<220> FEATURE:
<223> OTHER INFORMATION: polypeptide

<400> SEQUENCE: 37

His Ile Gly Lys Tyr Ile Leu Arg Trp Arg Pro Lys Gly Ser
1               5                   10

<210> SEQ ID NO 38
<211> LENGTH: 13
<212> TYPE: PRT
<213> ORGANISM: Artificial Sequence
<220> FEATURE:
<223> OTHER INFORMATION: polypeptide

<400> SEQUENCE: 38

His Ile Gly Lys Tyr Ile Leu Arg Trp Arg Pro Lys Gly
1               5                   10

<210> SEQ ID NO 39
<211> LENGTH: 15
<212> TYPE: PRT
<213> ORGANISM: Artificial Sequence
<220> FEATURE:
<223> OTHER INFORMATION: polypeptide

<400> SEQUENCE: 39

His Ile Ser Lys Tyr Gly Leu Arg Trp Arg Pro Lys Asn Ser Val
1               5                   10                  15

<210> SEQ ID NO 40
<211> LENGTH: 14
<212> TYPE: PRT
<213> ORGANISM: Artificial Sequence
<220> FEATURE:
<223> OTHER INFORMATION: polypeptide

<400> SEQUENCE: 40

His Ile Ser Lys Tyr Gly Leu Arg Trp Arg Pro Lys Asn Ser
1               5                   10

<210> SEQ ID NO 41
<211> LENGTH: 13
<212> TYPE: PRT
<213> ORGANISM: Artificial Sequence
<220> FEATURE:
<223> OTHER INFORMATION: polypeptide
```

<400> SEQUENCE: 41

His Ile Ser Lys Tyr Gly Leu Arg Trp Arg Pro Lys Asn
1               5                   10

<210> SEQ ID NO 42
<211> LENGTH: 15
<212> TYPE: PRT
<213> ORGANISM: Artificial Sequence
<220> FEATURE:
<223> OTHER INFORMATION: polypeptide

<400> SEQUENCE: 42

His Ile Ser Lys Tyr Gly Leu Arg Trp Arg Pro Lys Gly Ser Val
1               5                   10                  15

<210> SEQ ID NO 43
<211> LENGTH: 14
<212> TYPE: PRT
<213> ORGANISM: Artificial Sequence
<220> FEATURE:
<223> OTHER INFORMATION: polypeptide

<400> SEQUENCE: 43

His Ile Ser Lys Tyr Gly Leu Arg Trp Arg Pro Lys Gly Ser
1               5                   10

<210> SEQ ID NO 44
<211> LENGTH: 13
<212> TYPE: PRT
<213> ORGANISM: Artificial Sequence
<220> FEATURE:
<223> OTHER INFORMATION: polypeptide

<400> SEQUENCE: 44

His Ile Ser Lys Tyr Gly Leu Arg Trp Arg Pro Lys Gly
1               5                   10

<210> SEQ ID NO 45
<211> LENGTH: 14
<212> TYPE: PRT
<213> ORGANISM: Artificial Sequence
<220> FEATURE:
<223> OTHER INFORMATION: polypeptide

<400> SEQUENCE: 45

His Gly Ser Lys Tyr Gly Leu Arg Trp Arg Pro Lys Asn Ser
1               5                   10

<210> SEQ ID NO 46
<211> LENGTH: 13
<212> TYPE: PRT
<213> ORGANISM: Artificial Sequence
<220> FEATURE:
<223> OTHER INFORMATION: polypeptide

<400> SEQUENCE: 46

His Gly Ser Lys Tyr Gly Leu Arg Trp Arg Pro Lys Asn
1               5                   10

<210> SEQ ID NO 47
<211> LENGTH: 15
<212> TYPE: PRT
<213> ORGANISM: Artificial Sequence
<220> FEATURE:
<223> OTHER INFORMATION: polypeptide

```
<400> SEQUENCE: 47

His Gly Ser Lys Tyr Gly Leu Arg Trp Arg Pro Lys Gly Ser Val
1               5                   10                  15

<210> SEQ ID NO 48
<211> LENGTH: 14
<212> TYPE: PRT
<213> ORGANISM: Artificial Sequence
<220> FEATURE:
<223> OTHER INFORMATION: polypeptide

<400> SEQUENCE: 48

His Gly Ser Lys Tyr Gly Leu Arg Trp Arg Pro Lys Gly Ser
1               5                   10

<210> SEQ ID NO 49
<211> LENGTH: 13
<212> TYPE: PRT
<213> ORGANISM: Artificial Sequence
<220> FEATURE:
<223> OTHER INFORMATION: polypeptide

<400> SEQUENCE: 49

His Gly Ser Lys Tyr Gly Leu Arg Trp Arg Pro Lys Gly
1               5                   10

<210> SEQ ID NO 50
<211> LENGTH: 15
<212> TYPE: PRT
<213> ORGANISM: Artificial Sequence
<220> FEATURE:
<223> OTHER INFORMATION: polypeptide

<400> SEQUENCE: 50

His Leu Ser Lys Tyr Gly Leu Arg Trp Arg Pro Lys Asn Ser Val
1               5                   10                  15

<210> SEQ ID NO 51
<211> LENGTH: 14
<212> TYPE: PRT
<213> ORGANISM: Artificial Sequence
<220> FEATURE:
<223> OTHER INFORMATION: polypeptide

<400> SEQUENCE: 51

His Leu Ser Lys Tyr Gly Leu Arg Trp Arg Pro Lys Asn Ser
1               5                   10

<210> SEQ ID NO 52
<211> LENGTH: 13
<212> TYPE: PRT
<213> ORGANISM: Artificial Sequence
<220> FEATURE:
<223> OTHER INFORMATION: polypeptide

<400> SEQUENCE: 52

His Leu Ser Lys Tyr Gly Leu Arg Trp Arg Pro Lys Asn
1               5                   10

<210> SEQ ID NO 53
<211> LENGTH: 15
<212> TYPE: PRT
<213> ORGANISM: Artificial Sequence
<220> FEATURE:
<223> OTHER INFORMATION: polypeptide

<400> SEQUENCE: 53
```

His Leu Ser Lys Tyr Gly Leu Arg Trp Arg Pro Lys Gly Ser Val
1               5                   10                  15

<210> SEQ ID NO 54
<211> LENGTH: 14
<212> TYPE: PRT
<213> ORGANISM: Artificial Sequence
<220> FEATURE:
<223> OTHER INFORMATION: polypeptide

<400> SEQUENCE: 54

His Leu Ser Lys Tyr Gly Leu Arg Trp Arg Pro Lys Gly Ser
1               5                   10

<210> SEQ ID NO 55
<211> LENGTH: 13
<212> TYPE: PRT
<213> ORGANISM: Artificial Sequence
<220> FEATURE:
<223> OTHER INFORMATION: polypeptide

<400> SEQUENCE: 55

His Leu Ser Lys Tyr Gly Leu Arg Trp Arg Pro Lys Gly
1               5                   10

<210> SEQ ID NO 56
<211> LENGTH: 14
<212> TYPE: PRT
<213> ORGANISM: Artificial Sequence
<220> FEATURE:
<223> OTHER INFORMATION: polypeptide

<400> SEQUENCE: 56

His Ile Gly Lys Tyr Gly Leu Arg Trp Arg Pro Lys Asn Ser
1               5                   10

<210> SEQ ID NO 57
<211> LENGTH: 13
<212> TYPE: PRT
<213> ORGANISM: Artificial Sequence
<220> FEATURE:
<223> OTHER INFORMATION: polypeptide

<400> SEQUENCE: 57

His Ile Gly Lys Tyr Gly Leu Arg Trp Arg Pro Lys Asn
1               5                   10

<210> SEQ ID NO 58
<211> LENGTH: 14
<212> TYPE: PRT
<213> ORGANISM: Artificial Sequence
<220> FEATURE:
<223> OTHER INFORMATION: polypeptide

<400> SEQUENCE: 58

His Ile Gly Lys Tyr Gly Leu Arg Trp Arg Pro Lys Gly Ser
1               5                   10

<210> SEQ ID NO 59
<211> LENGTH: 13
<212> TYPE: PRT
<213> ORGANISM: Artificial Sequence
<220> FEATURE:
<223> OTHER INFORMATION: polypeptide

<400> SEQUENCE: 59

His Ile Gly Lys Tyr Gly Leu Arg Trp Arg Pro Lys Gly
1               5                   10

<210> SEQ ID NO 60
<211> LENGTH: 15
<212> TYPE: PRT
<213> ORGANISM: Artificial Sequence
<220> FEATURE:
<223> OTHER INFORMATION: polypeptide

<400> SEQUENCE: 60

His Ile Ser Lys Tyr Leu Leu Arg Trp Arg Pro Lys Asn Ser Val
1               5                   10                  15

<210> SEQ ID NO 61
<211> LENGTH: 14
<212> TYPE: PRT
<213> ORGANISM: Artificial Sequence
<220> FEATURE:
<223> OTHER INFORMATION: polypeptide

<400> SEQUENCE: 61

His Ile Ser Lys Tyr Leu Leu Arg Trp Arg Pro Lys Asn Ser
1               5                   10

<210> SEQ ID NO 62
<211> LENGTH: 13
<212> TYPE: PRT
<213> ORGANISM: Artificial Sequence
<220> FEATURE:
<223> OTHER INFORMATION: polypeptide

<400> SEQUENCE: 62

His Ile Ser Lys Tyr Leu Leu Arg Trp Arg Pro Lys Asn
1               5                   10

<210> SEQ ID NO 63
<211> LENGTH: 15
<212> TYPE: PRT
<213> ORGANISM: Artificial Sequence
<220> FEATURE:
<223> OTHER INFORMATION: polypeptide

<400> SEQUENCE: 63

His Ile Ser Lys Tyr Leu Leu Arg Trp Arg Pro Lys Gly Ser Val
1               5                   10                  15

<210> SEQ ID NO 64
<211> LENGTH: 14
<212> TYPE: PRT
<213> ORGANISM: Artificial Sequence
<220> FEATURE:
<223> OTHER INFORMATION: polypeptide

<400> SEQUENCE: 64

His Ile Ser Lys Tyr Leu Leu Arg Trp Arg Pro Lys Gly Ser
1               5                   10

<210> SEQ ID NO 65
<211> LENGTH: 13
<212> TYPE: PRT
<213> ORGANISM: Artificial Sequence
<220> FEATURE:
<223> OTHER INFORMATION: polypeptide

<400> SEQUENCE: 65

His Ile Ser Lys Tyr Leu Leu Arg Trp Arg Pro Lys Gly

```
<210> SEQ ID NO 66
<211> LENGTH: 15
<212> TYPE: PRT
<213> ORGANISM: Artificial Sequence
<220> FEATURE:
<223> OTHER INFORMATION: polypeptide

<400> SEQUENCE: 66

His Gly Ser Lys Tyr Leu Leu Arg Trp Arg Pro Lys Asn Ser Val
1               5                   10                  15

<210> SEQ ID NO 67
<211> LENGTH: 14
<212> TYPE: PRT
<213> ORGANISM: Artificial Sequence
<220> FEATURE:
<223> OTHER INFORMATION: polypeptide

<400> SEQUENCE: 67

His Gly Ser Lys Tyr Leu Leu Arg Trp Arg Pro Lys Asn Ser
1               5                   10

<210> SEQ ID NO 68
<211> LENGTH: 13
<212> TYPE: PRT
<213> ORGANISM: Artificial Sequence
<220> FEATURE:
<223> OTHER INFORMATION: polypeptide

<400> SEQUENCE: 68

His Gly Ser Lys Tyr Leu Leu Arg Trp Arg Pro Lys Asn
1               5                   10

<210> SEQ ID NO 69
<211> LENGTH: 15
<212> TYPE: PRT
<213> ORGANISM: Artificial Sequence
<220> FEATURE:
<223> OTHER INFORMATION: polypeptide

<400> SEQUENCE: 69

His Gly Ser Lys Tyr Leu Leu Arg Trp Arg Pro Lys Gly Ser Val
1               5                   10                  15

<210> SEQ ID NO 70
<211> LENGTH: 14
<212> TYPE: PRT
<213> ORGANISM: Artificial Sequence
<220> FEATURE:
<223> OTHER INFORMATION: polypeptide

<400> SEQUENCE: 70

His Gly Ser Lys Tyr Leu Leu Arg Trp Arg Pro Lys Gly Ser
1               5                   10

<210> SEQ ID NO 71
<211> LENGTH: 13
<212> TYPE: PRT
<213> ORGANISM: Artificial Sequence
<220> FEATURE:
<223> OTHER INFORMATION: polypeptide

<400> SEQUENCE: 71

His Gly Ser Lys Tyr Leu Leu Arg Trp Arg Pro Lys Gly
1               5                   10
```

<210> SEQ ID NO 72
<211> LENGTH: 15
<212> TYPE: PRT
<213> ORGANISM: Artificial Sequence
<220> FEATURE:
<223> OTHER INFORMATION: polypeptide

<400> SEQUENCE: 72

His Leu Ser Lys Tyr Leu Leu Arg Trp Arg Pro Lys Asn Ser Val
1               5                   10                  15

<210> SEQ ID NO 73
<211> LENGTH: 14
<212> TYPE: PRT
<213> ORGANISM: Artificial Sequence
<220> FEATURE:
<223> OTHER INFORMATION: polypeptide

<400> SEQUENCE: 73

His Leu Ser Lys Tyr Leu Leu Arg Trp Arg Pro Lys Asn Ser
1               5                   10

<210> SEQ ID NO 74
<211> LENGTH: 13
<212> TYPE: PRT
<213> ORGANISM: Artificial Sequence
<220> FEATURE:
<223> OTHER INFORMATION: polypeptide

<400> SEQUENCE: 74

His Leu Ser Lys Tyr Leu Leu Arg Trp Arg Pro Lys Asn
1               5                   10

<210> SEQ ID NO 75
<211> LENGTH: 15
<212> TYPE: PRT
<213> ORGANISM: Artificial Sequence
<220> FEATURE:
<223> OTHER INFORMATION: polypeptide

<400> SEQUENCE: 75

His Leu Ser Lys Tyr Leu Leu Arg Trp Arg Pro Lys Gly Ser Val
1               5                   10                  15

<210> SEQ ID NO 76
<211> LENGTH: 14
<212> TYPE: PRT
<213> ORGANISM: Artificial Sequence
<220> FEATURE:
<223> OTHER INFORMATION: polypeptide

<400> SEQUENCE: 76

His Leu Ser Lys Tyr Leu Leu Arg Trp Arg Pro Lys Gly Ser
1               5                   10

<210> SEQ ID NO 77
<211> LENGTH: 13
<212> TYPE: PRT
<213> ORGANISM: Artificial Sequence
<220> FEATURE:
<223> OTHER INFORMATION: polypeptide

<400> SEQUENCE: 77

His Leu Ser Lys Tyr Leu Leu Arg Trp Arg Pro Lys Gly
1               5                   10

```
<210> SEQ ID NO 78
<211> LENGTH: 15
<212> TYPE: PRT
<213> ORGANISM: Artificial Sequence
<220> FEATURE:
<223> OTHER INFORMATION: polypeptide

<400> SEQUENCE: 78

His Ile Gly Lys Tyr Leu Leu Arg Trp Arg Pro Lys Asn Ser Val
1               5                   10                  15

<210> SEQ ID NO 79
<211> LENGTH: 14
<212> TYPE: PRT
<213> ORGANISM: Artificial Sequence
<220> FEATURE:
<223> OTHER INFORMATION: polypeptide

<400> SEQUENCE: 79

His Ile Gly Lys Tyr Leu Leu Arg Trp Arg Pro Lys Asn Ser
1               5                   10

<210> SEQ ID NO 80
<211> LENGTH: 13
<212> TYPE: PRT
<213> ORGANISM: Artificial Sequence
<220> FEATURE:
<223> OTHER INFORMATION: polypeptide

<400> SEQUENCE: 80

His Ile Gly Lys Tyr Leu Leu Arg Trp Arg Pro Lys Asn
1               5                   10

<210> SEQ ID NO 81
<211> LENGTH: 15
<212> TYPE: PRT
<213> ORGANISM: Artificial Sequence
<220> FEATURE:
<223> OTHER INFORMATION: polypeptide

<400> SEQUENCE: 81

His Ile Gly Lys Tyr Leu Leu Arg Trp Arg Pro Lys Gly Ser Val
1               5                   10                  15

<210> SEQ ID NO 82
<211> LENGTH: 14
<212> TYPE: PRT
<213> ORGANISM: Artificial Sequence
<220> FEATURE:
<223> OTHER INFORMATION: polypeptide

<400> SEQUENCE: 82

His Ile Gly Lys Tyr Leu Leu Arg Trp Arg Pro Lys Gly Ser
1               5                   10

<210> SEQ ID NO 83
<211> LENGTH: 13
<212> TYPE: PRT
<213> ORGANISM: Artificial Sequence
<220> FEATURE:
<223> OTHER INFORMATION: polypeptide

<400> SEQUENCE: 83

His Ile Gly Lys Tyr Leu Leu Arg Trp Arg Pro Lys Gly
1               5                   10
```

```
<210> SEQ ID NO 84
<211> LENGTH: 15
<212> TYPE: PRT
<213> ORGANISM: Artificial Sequence
<220> FEATURE:
<223> OTHER INFORMATION: polypeptide

<400> SEQUENCE: 84

His Ile Ser Lys Tyr Ile Gly Arg Trp Arg Pro Lys Asn Ser Val
1               5                   10                  15

<210> SEQ ID NO 85
<211> LENGTH: 14
<212> TYPE: PRT
<213> ORGANISM: Artificial Sequence
<220> FEATURE:
<223> OTHER INFORMATION: polypeptide

<400> SEQUENCE: 85

His Ile Ser Lys Tyr Ile Gly Arg Trp Arg Pro Lys Asn Ser
1               5                   10

<210> SEQ ID NO 86
<211> LENGTH: 13
<212> TYPE: PRT
<213> ORGANISM: Artificial Sequence
<220> FEATURE:
<223> OTHER INFORMATION: polypeptide

<400> SEQUENCE: 86

His Ile Ser Lys Tyr Ile Gly Arg Trp Arg Pro Lys Asn
1               5                   10

<210> SEQ ID NO 87
<211> LENGTH: 15
<212> TYPE: PRT
<213> ORGANISM: Artificial Sequence
<220> FEATURE:
<223> OTHER INFORMATION: polypeptide

<400> SEQUENCE: 87

His Ile Ser Lys Tyr Ile Gly Arg Trp Arg Pro Lys Gly Ser Val
1               5                   10                  15

<210> SEQ ID NO 88
<211> LENGTH: 14
<212> TYPE: PRT
<213> ORGANISM: Artificial Sequence
<220> FEATURE:
<223> OTHER INFORMATION: polypeptide

<400> SEQUENCE: 88

His Ile Ser Lys Tyr Ile Gly Arg Trp Arg Pro Lys Gly Ser
1               5                   10

<210> SEQ ID NO 89
<211> LENGTH: 13
<212> TYPE: PRT
<213> ORGANISM: Artificial Sequence
<220> FEATURE:
<223> OTHER INFORMATION: polypeptide

<400> SEQUENCE: 89

His Ile Ser Lys Tyr Ile Gly Arg Trp Arg Pro Lys Gly
1               5                   10

<210> SEQ ID NO 90
```

```
<211> LENGTH: 14
<212> TYPE: PRT
<213> ORGANISM: Artificial Sequence
<220> FEATURE:
<223> OTHER INFORMATION: polypeptide

<400> SEQUENCE: 90

His Gly Ser Lys Tyr Ile Gly Arg Trp Arg Pro Lys Asn Ser
1               5                   10

<210> SEQ ID NO 91
<211> LENGTH: 13
<212> TYPE: PRT
<213> ORGANISM: Artificial Sequence
<220> FEATURE:
<223> OTHER INFORMATION: polypeptide

<400> SEQUENCE: 91

His Gly Ser Lys Tyr Ile Gly Arg Trp Arg Pro Lys Asn
1               5                   10

<210> SEQ ID NO 92
<211> LENGTH: 14
<212> TYPE: PRT
<213> ORGANISM: Artificial Sequence
<220> FEATURE:
<223> OTHER INFORMATION: polypeptide

<400> SEQUENCE: 92

His Gly Ser Lys Tyr Ile Gly Arg Trp Arg Pro Lys Gly Ser
1               5                   10

<210> SEQ ID NO 93
<211> LENGTH: 13
<212> TYPE: PRT
<213> ORGANISM: Artificial Sequence
<220> FEATURE:
<223> OTHER INFORMATION: polypeptide

<400> SEQUENCE: 93

His Gly Ser Lys Tyr Ile Gly Arg Trp Arg Pro Lys Gly
1               5                   10

<210> SEQ ID NO 94
<211> LENGTH: 15
<212> TYPE: PRT
<213> ORGANISM: Artificial Sequence
<220> FEATURE:
<223> OTHER INFORMATION: polypeptide

<400> SEQUENCE: 94

His Leu Ser Lys Tyr Ile Gly Arg Trp Arg Pro Lys Asn Ser Val
1               5                   10                  15

<210> SEQ ID NO 95
<211> LENGTH: 14
<212> TYPE: PRT
<213> ORGANISM: Artificial Sequence
<220> FEATURE:
<223> OTHER INFORMATION: polypeptide

<400> SEQUENCE: 95

His Leu Ser Lys Tyr Ile Gly Arg Trp Arg Pro Lys Asn Ser
1               5                   10

<210> SEQ ID NO 96
<211> LENGTH: 13
```

```
<212> TYPE: PRT
<213> ORGANISM: Artificial Sequence
<220> FEATURE:
<223> OTHER INFORMATION: polypeptide

<400> SEQUENCE: 96

His Leu Ser Lys Tyr Ile Gly Arg Trp Arg Pro Lys Asn
1               5                   10

<210> SEQ ID NO 97
<211> LENGTH: 15
<212> TYPE: PRT
<213> ORGANISM: Artificial Sequence
<220> FEATURE:
<223> OTHER INFORMATION: polypeptide

<400> SEQUENCE: 97

His Leu Ser Lys Tyr Ile Gly Arg Trp Arg Pro Lys Gly Ser Val
1               5                   10                  15

<210> SEQ ID NO 98
<211> LENGTH: 14
<212> TYPE: PRT
<213> ORGANISM: Artificial Sequence
<220> FEATURE:
<223> OTHER INFORMATION: polypeptide

<400> SEQUENCE: 98

His Leu Ser Lys Tyr Ile Gly Arg Trp Arg Pro Lys Gly Ser
1               5                   10

<210> SEQ ID NO 99
<211> LENGTH: 13
<212> TYPE: PRT
<213> ORGANISM: Artificial Sequence
<220> FEATURE:
<223> OTHER INFORMATION: polypeptide

<400> SEQUENCE: 99

His Leu Ser Lys Tyr Ile Gly Arg Trp Arg Pro Lys Gly
1               5                   10

<210> SEQ ID NO 100
<211> LENGTH: 14
<212> TYPE: PRT
<213> ORGANISM: Artificial Sequence
<220> FEATURE:
<223> OTHER INFORMATION: polypeptide

<400> SEQUENCE: 100

His Ile Gly Lys Tyr Ile Gly Arg Trp Arg Pro Lys Asn Ser
1               5                   10

<210> SEQ ID NO 101
<211> LENGTH: 13
<212> TYPE: PRT
<213> ORGANISM: Artificial Sequence
<220> FEATURE:
<223> OTHER INFORMATION: polypeptide

<400> SEQUENCE: 101

His Ile Gly Lys Tyr Ile Gly Arg Trp Arg Pro Lys Asn
1               5                   10

<210> SEQ ID NO 102
<211> LENGTH: 15
<212> TYPE: PRT
```

```
<213> ORGANISM: Artificial Sequence
<220> FEATURE:
<223> OTHER INFORMATION: polypeptide

<400> SEQUENCE: 102

His Ile Gly Lys Tyr Ile Gly Arg Trp Arg Pro Lys Gly Ser Val
1               5                   10                  15

<210> SEQ ID NO 103
<211> LENGTH: 14
<212> TYPE: PRT
<213> ORGANISM: Artificial Sequence
<220> FEATURE:
<223> OTHER INFORMATION: polypeptide

<400> SEQUENCE: 103

His Ile Gly Lys Tyr Ile Gly Arg Trp Arg Pro Lys Gly Ser
1               5                   10

<210> SEQ ID NO 104
<211> LENGTH: 13
<212> TYPE: PRT
<213> ORGANISM: Artificial Sequence
<220> FEATURE:
<223> OTHER INFORMATION: polypeptide

<400> SEQUENCE: 104

His Ile Gly Lys Tyr Ile Gly Arg Trp Arg Pro Lys Gly
1               5                   10

<210> SEQ ID NO 105
<211> LENGTH: 9
<212> TYPE: PRT
<213> ORGANISM: Artificial Sequence
<220> FEATURE:
<223> OTHER INFORMATION: extra C- or N-terminal aminoacids

<400> SEQUENCE: 105

Thr Ser His His His His His His Cys
1               5

<210> SEQ ID NO 106
<211> LENGTH: 18
<212> TYPE: PRT
<213> ORGANISM: Artificial Sequence
<220> FEATURE:
<223> OTHER INFORMATION: polypeptide having a polylysine linker

<400> SEQUENCE: 106

Lys Lys Lys His Ile Gly Lys Tyr Gly Leu Arg Trp Arg Pro Lys Gly
1               5                   10                  15

Ser Val

<210> SEQ ID NO 107
<211> LENGTH: 18
<212> TYPE: PRT
<213> ORGANISM: Artificial Sequence
<220> FEATURE:
<223> OTHER INFORMATION: polypeptide having a polylysine linker

<400> SEQUENCE: 107

His Ile Gly Lys Tyr Gly Leu Arg Trp Arg Pro Lys Gly Ser Val Lys
1               5                   10                  15

Lys Lys
```

```
<210> SEQ ID NO 108
<211> LENGTH: 14
<212> TYPE: PRT
<213> ORGANISM: Artificial Sequence
<220> FEATURE:
<223> OTHER INFORMATION: P12 fragment 1

<400> SEQUENCE: 108

Pro Ser His Ile Ser Lys Tyr Ile Leu Arg Trp Arg Pro Lys
1               5                   10

<210> SEQ ID NO 109
<211> LENGTH: 14
<212> TYPE: PRT
<213> ORGANISM: Artificial Sequence
<220> FEATURE:
<223> OTHER INFORMATION: P12 fragment 2

<400> SEQUENCE: 109

His Ile Ser Lys Tyr Ile Leu Arg Trp Arg Pro Lys Pro Ser
1               5                   10

<210> SEQ ID NO 110
<211> LENGTH: 14
<212> TYPE: PRT
<213> ORGANISM: Artificial Sequence
<220> FEATURE:
<223> OTHER INFORMATION: P12 fragment 3

<400> SEQUENCE: 110

Lys Tyr Ile Leu Arg Trp Arg Pro Lys Pro Ser His Ile Ser
1               5                   10

<210> SEQ ID NO 111
<211> LENGTH: 14
<212> TYPE: PRT
<213> ORGANISM: Artificial Sequence
<220> FEATURE:
<223> OTHER INFORMATION: P12 fragment 4

<400> SEQUENCE: 111

Leu Arg Trp Arg Pro Lys Pro Ser His Ile Ser Lys Tyr Ile
1               5                   10

<210> SEQ ID NO 112
<211> LENGTH: 14
<212> TYPE: PRT
<213> ORGANISM: Artificial Sequence
<220> FEATURE:
<223> OTHER INFORMATION: P12 fragment 5

<400> SEQUENCE: 112

Arg Trp Arg Pro Lys Pro Ser His Ile Ser Lys Tyr Ile Leu
1               5                   10
```

PEPTIDES DERIVED FROM FIBRONECTIN WITH IMPROVED BIOACTIVITY AND REDUCED SUSCEPTIBILITY TO NEUTROPHIL ELASTASE DEGRADATION

GOVERNMENT SUPPORT

This invention was made with government support awarded by US Army AFIRM 1 and JWMRP S14 under grant numbers W81XWH-08-2-0034 and W81XWH-15-C-0043, respectively. The government has certain rights in the invention.

STATEMENT REGARDING ELECTRONIC FILING OF A SEQUENCE LISTING

A Sequence Listing in ASCII text format, submitted under 37 C.F.R. § 1.821, entitled 1543-3_ST25.txt, 27,862 bytes in size, generated on Feb. 11, 2020 and filed via EFS-Web, is provided in lieu of a paper copy. This Sequence Listing is hereby incorporated by reference herein into the specification for its disclosures.

TECHNICAL FIELD

This invention is based on the discovery of polypeptides derived from fibronectin that are neutrophil elastase-resistant and can bind to growth factors and/or enhance growth factor activity. Previously known polypeptides derived from fibronectin with the ability to enhance growth factor activity are found to be susceptible to degradation by human neutrophil elastase, reducing their effectiveness in in vivo uses. This invention relates to novel growth factor enhancing polypeptides with increased resistance to degradation by neutrophil elastase. This invention also relates to the uses of such compounds in cosmetic treatments and the treatment of wounds and cancer.

BACKGROUND

In the US civilian population, each year, approximately 500,000 patients with burns present to emergency departments. Of 40,000 annual hospital admissions, 25,000 burn victims are admitted to specialized burn centers. Progressive extension of burns can have a devastating effect. Over the course of a few days to one week deep partial-thickness burns can become full-thickness burns, which in the short term, leads to increased tissue loss, longer healing time, excess morbidity and mortality. In the long term, increased scarring, wound contractures and poor quality of life become major issues. While the exact mechanism(s) leading to conversion of the zone of ischemia to full-blown necrosis is unclear, several processes, including oxidant and cytokine stress resulting from inflammation as well as ischemia/reperfusion, probably play a role. Therapies to improve blood flow, such as non-steroidal anti-inflammatory agents (NSAIDS) and anti-coagulants (heparin) have not shown substantial benefit in preventing burn injury progression. Hence therapy to limit burn injury progression is an unmet need. There is evidence that fibronectin (FN) is involved in many biological processes including tissue repair, embryogenesis, blood clotting, cell migration, wound repair, and cell adhesion. There are two primary forms of fibronectin. The first is an insoluble glycoprotein dimer that serves as a linker in the extracellular matrix (ECM), and the second is a soluble disulfide-linked dimer found in plasma. The ECM form of fibronectin is expressed by fibroblasts, chondrocytes, endothelial cells, macrophages and certain epithelial cells. The plasma form of fibronectin is expressed by hepatocytes. Fibronectin can serve as a general cell adhesion molecule by anchoring cells to collagen or to proteoglycan substrates. Fibronectin can also play a role in organizing cellular interactions by binding to components of the ECM and to membrane-bound fibronectin receptors on cell surfaces. Forms of fibronectin are found in vertebrates, including mammals, birds, amphibians, fish, and reptiles.

FN, a 500 kDa glycoprotein, circulates in the blood and is produced and deposited by tissue cells in the provisional extracellular matrix (ECM) during tissue formation. As a critical component of the provisional ECM, FN plays a vital role in embryogenesis, morphogenesis and wound healing but is deficient in burn patients' wounds and blood. FN is known to be degraded in burn wound fluids by the endopeptidase neutrophil elastase. See Grinnell, et al., *Identification of Neutrophil Elastase as the Proteinase in Burn Wound Fluid Responsible for Degradation of Fibronectin*, J Invest. Dermatology, 1994, 103(2):155-61.

Previously disclosed peptide "P12" is 14-residue peptide that is cryptic within the immunoglobulin sandwich type of β-pleated sheet of fibronectin's (FN) first type III repeat (FNIII$_1$). Unlike FN, P12 in solution promotes mesenchymal cell growth, proliferation and migration intrinsically and synergistically with a variety of growth factors, especially platelet-derived growth factor-BB (PDGF-BB). Furthermore, P12 protects adult human dermal fibroblasts (AHDF) from cell death induced by oxidative and cytokine stress and/or nutrient withdrawal in the presence of PDGF-BB. P12 also limits burn injury progression in rat and porcine burn models and mitigates scarring in a vertical burn injury progression pig model. See, e.g., PCT/US2006/038778; U.S. Pat. No. 8,759,300; Lin, et al., *Fibronectin peptides that bind PDGF-BB enhance survival of cells and tissue under stress*, J Invest Dermatol. 2014 April; 134(4): 1119-1127; and Asif, et al., *Blood Vessel Occlusion in Peri-burn Tissue is Secondary to Erythrocyte Aggregation and Mitigated by a Fibronectin-derived Peptide that Limits Burn Injury Progression*, Wound Rep Reg (2016) 24 501-513. In particular, the fragment of fibronectin PSHISKYILRWRPK (SEQ ID NO:108), or "P12" is disclosed in both Lin, et al. and Asif, et al. as being useful for the treatment of wounds, particularly the treatment of burns.

SUMMARY

We present neutrophil elastate-resistant peptides derived from fragments of fibronectin for use in the treatment of wounds. In particular, we have discovered that previously disclosed, biologically active, peptide fragments of fibronectin, such as P12, are readily degraded, in vitro, by neutrophil elastase, and do not promote healing when applied topically to wounds. Even cyclized forms of the previously disclosed, biologically active, peptide fragments of fibronectin, such as cyclic P12, remain sensitive to this endopeptidase. We present peptides that are fragments and/or derivatives of fragments of fibronectin that maintain their biological activity of binding growth factors, such as platelet-derived growth factor-BB (PDGF-BB) and enhancing fibroblast survival, and also have been modified to increase their resistance to degradation by neutrophil elastase, in vitro and in vivo.

In some embodiments of the invention, the neutrophil elastase resistant peptide is a linear or cyclic polypeptide according to formula I:

(I):
(SEQ ID NO: 1)
H-X$_1$-X$_2$-K-Y-X$_3$-X$_4$-R-W-R-P-K-X$_5$-X$_6$-X$_7$ wherein X$_1$ is I or G or L,
X$_2$ is S or G,
X$_3$ is I or G or L,
X$_4$ is L or G,
X$_5$ is N or G,
X$_6$ is absent or S, and
X$_7$ is absent or V; and
wherein no two consecutive amino acids in the first 13 amino acids of the polypeptide differ from the sequence HISKYILRWRPKN (SEQ ID NO:9). An embodiment of this invention wherein X$_6$ of formula I is absent is set forth in the Sequence Listing as SEQ ID NO:2. An embodiment of this invention wherein X$_6$ and X$_7$ of formula I are absent is set forth in the Sequence Listing as SEQ ID NO:3. An embodiment of this invention wherein X$_7$ of formula I is absent is set forth in the Sequence Listing as SEQ ID NO:4.

Further embodiments of the invention include HISKYILRWRPKNSV (SEQ ID NO:10) (P46), HIGKYGLRWRPKNSV (SEQ ID NO:11) (cNP7), HIGKYGLRWRPKGSV (SEQ ID NO:12) (cNP8), HGSKYGLRWRPKNSV (SEQ ID NO:13), HIGKYIGRWRPKNSV (SEQ ID NO:14), HGSKYIGRWRPKNSV (SEQ ID NO:15), HGSKYIGRWRPKGSV (SEQ ID NO:16) and cyclic forms thereof.

We also present methods of using these peptides for cosmetic treatments and the treatment of wounds and cardiovascular disease. The wounds to be treated include surgical incision or extirpation, a traumatic injury, a thermal burn, a chemical burn, a lesion or ulceration of the patient's skin, mucosa, connective tissue, fascia, ligament, tendon, cartilage, nerve or muscle and a wound to the patient's bone. The treated wounds may be infected or uninfected. The cardiovascular incidents to be treated include blood vessels occluded with aggregates of red blood cell and/or fibrinogen and/or fibrin, such as can occur in burn wounds; myocardial infarction; multi-organ failure; diabetes; sickle cell anemia; polycythemia vera; and hyperfibrinogenemia. In a particular embodiment, the neutrophil elastase resistant peptides of the invention are used to treat thermal and/or chemical burns.

The invention also features compositions (e.g., physiologically acceptable compositions) that include a neutrophil elastase resistant peptide of the invention. The physiologically acceptable composition may be a pharmaceutical composition that promotes a therapeutic response. As noted above, cosmetic compositions are also featured and can include the peptides described herein. The present compositions may also be non-pharmaceutical in the sense that they may include concentrated peptides and/or other ingredients that should be diluted or otherwise modified (e.g., mixed with other active or inactive ingredients) prior to use (e.g., in cell culture or as a cosmetic or therapeutic formulation).

BRIEF DESCRIPTION OF THE DRAWINGS

FIG. 1A: cP12 was incubated with purified human neutrophil elastase at 1:200 enzyme: substrate molar ratio, minimal intact peptide (MW=1789) was retained at 24 h. FIG. 1B: Elastase sensitive sites of cP12 cleaved by human neutrophil elastase and analyzed by MS. PSHISKYILRWRPK is SEQ ID NO:108; HISKYILPWRPKPS is SEQ ID NO:109; KYILRWRPKP-SHIS is SEQ ID NO:110; LRWRKPSHISKYI is SEQ ID NO:111; and RWRPKPSHISKYIL is SEQ ID NO:112.

DETAILED DESCRIPTION

The details of one or more embodiments of the invention are set forth in the accompanying drawings and the description below. Other features, objects, and advantages of the invention will be apparent from the description and drawings, and from the claims.

Figure 1A:
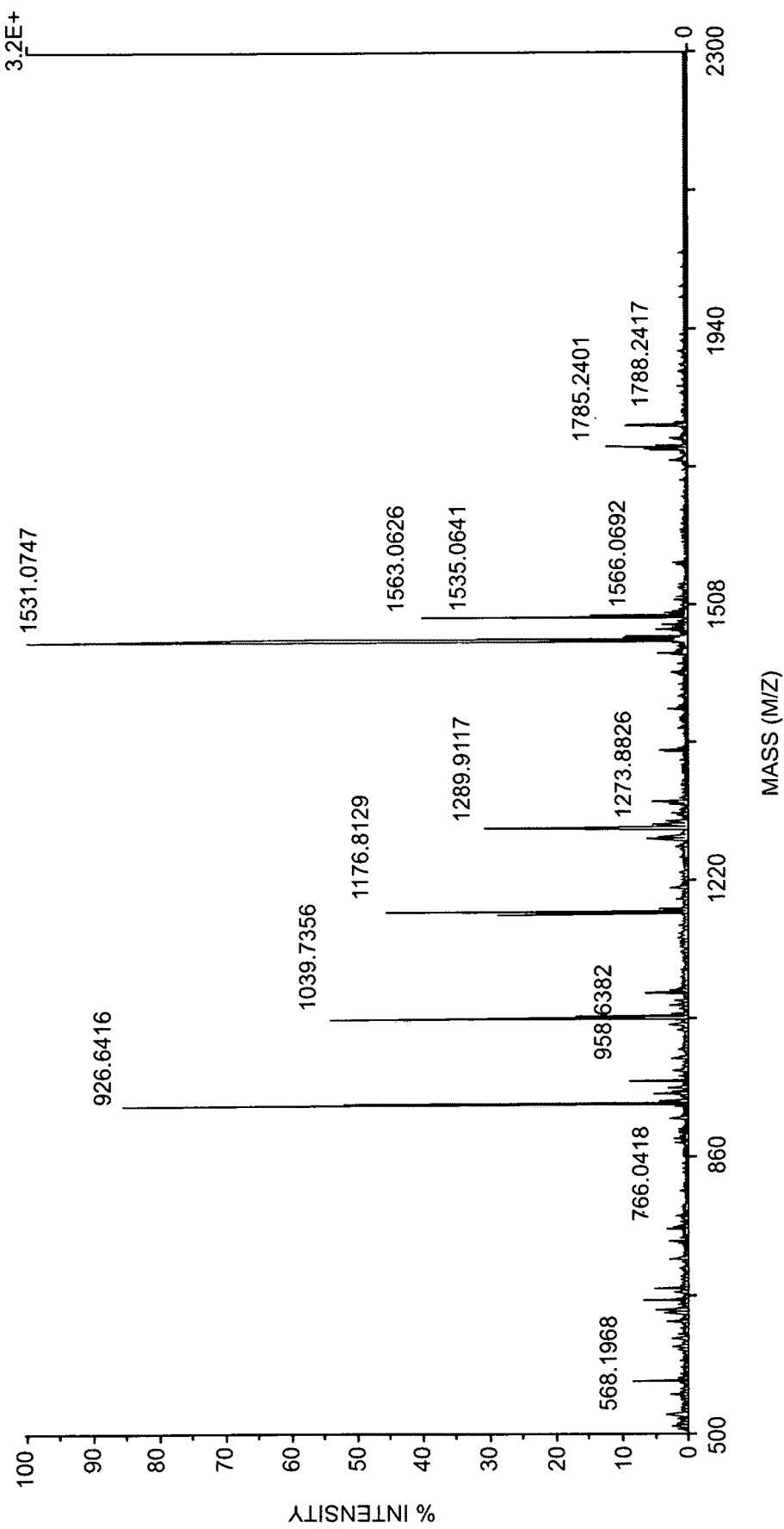
FIGS. 1A-1B show a diagram of the susceptibility of cP12 to digestion by human neutrophil elastase.
Figure 1B:

Determination of Peptides Derived from Fibronectin with Improved Bioactivity and Resistance to Neutrophil Elastase Digestion Previously disclosed peptide P12 is degraded by neutrophil elastase, which is present in wound fluids: To determine whether cyclic P12 ("cP12") is sensitive to endopeptidases, cP12 was digested with human neutrophil elastase. The reaction was stopped with formic acid and the reaction mixture was analyzed by mass spectroscopy. Analysis of results showed that cP12 has five elastase-cleavage sites (FIG. 1B). In addition, almost all intact cP12 substrate (1789 mw) was eliminated (FIG. 1A).

Figure 2:
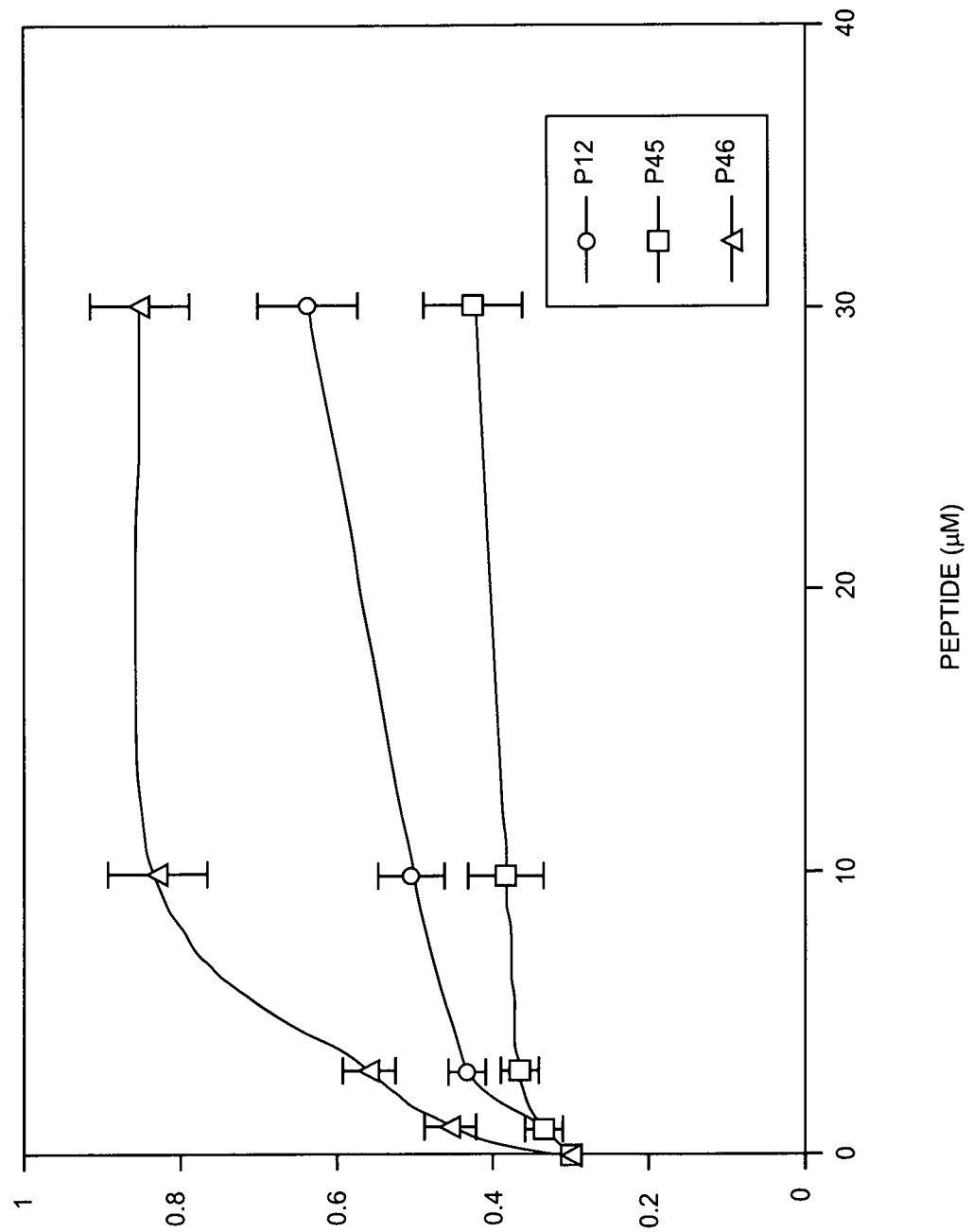
FIG. 2 shows bioactivity for P12, P45 and P46. Adult human dermal fibroblasts CF31 cells at 1000 cells/well were seeded in a collagen-coated 96-well plate in DMEM overnight, then 1 nM PDGF-BB with peptides at indicated doses was added and cells were incubated at 37° C. for 6 days. Then cell metabolism was measured by XTT assay by reading OD at 450 nm. Each point represents the mean of 6 replicates with a typical SD=5-10% around the mean (not shown for graft clarity).

Determination of Fragments Created by Digestion of Fibronectin with Human Neutrophil Elastase, and Their Bioactivity To find an elastase-resistant cP12-derivative with cP12-equivalent bioactivity, we digested fibronectin III$_1$-C (FNIII$_1$-C), in which P12 peptide is found, with purified human neutrophil elastase at 1:100 enzyme:substrate molar ratio at 37° C. for 4 h or 24 h. Digested samples were analyzed with MS. The results at both time points showed that elastase digestion of FN III$_1$-C produced two peptides, P45 (SKYILRWRPKNSV) (SEQ ID NO:5) and P46 (HISKYILRWRPKNSV) (SEQ ID NO:10) from the same region of fibronectin as P12. Bioactivity assay demonstrated that P46 showed higher bioactivity than P12 as determined by fibroblast metabolism assay (FIG. 2). On the other hand, P45 showed little bioactivity (FIG. 2).

Determination of Sensitivity of P46 to Human Neutrophil Elastase Digestion

Figure 3A:
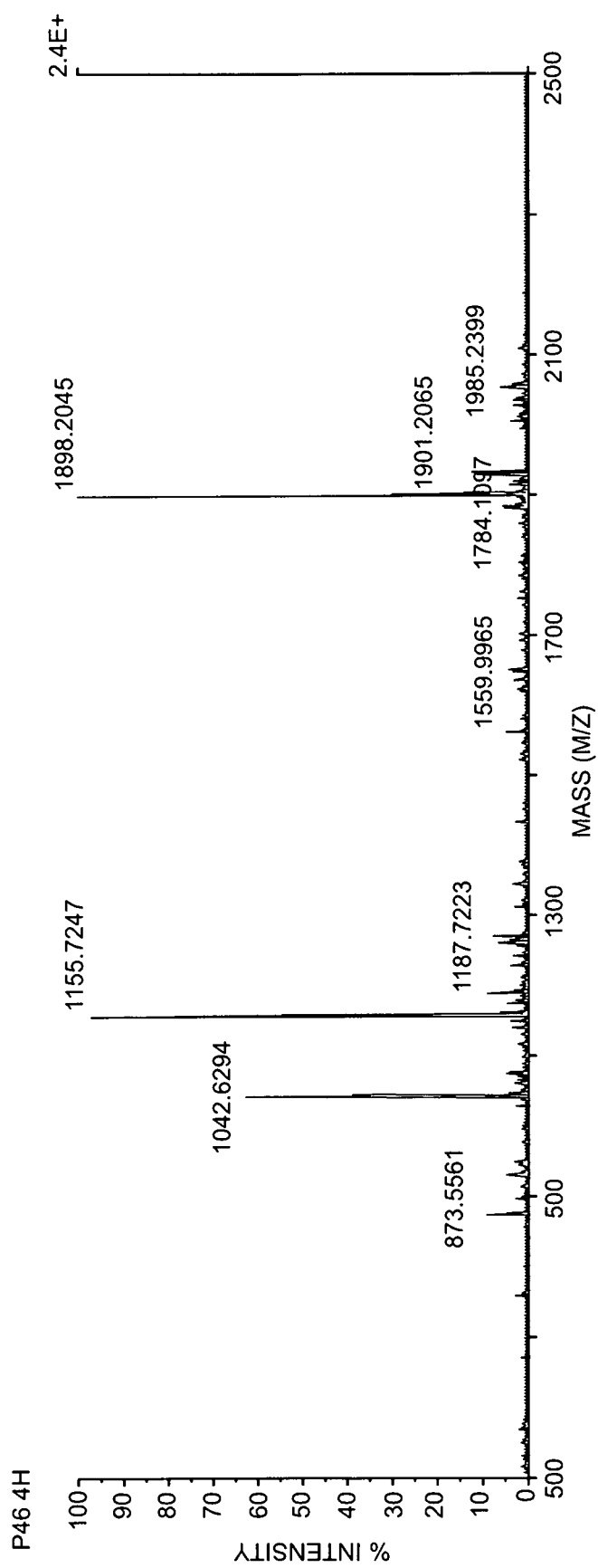
FIGS. 3A-3B show P46 digestion by neutrophil elastase at 4 hours and 24 hours. P46 was incubated with purified human neutrophil elastase at 1:100 enzyme:substrate molar ratio at 37° C. for 4 h (3A) or 24 h (3B). Peptides stability was determined by MALDI-TOF analysis. Molecular weight of P46 is 1898.
Figure 3B:
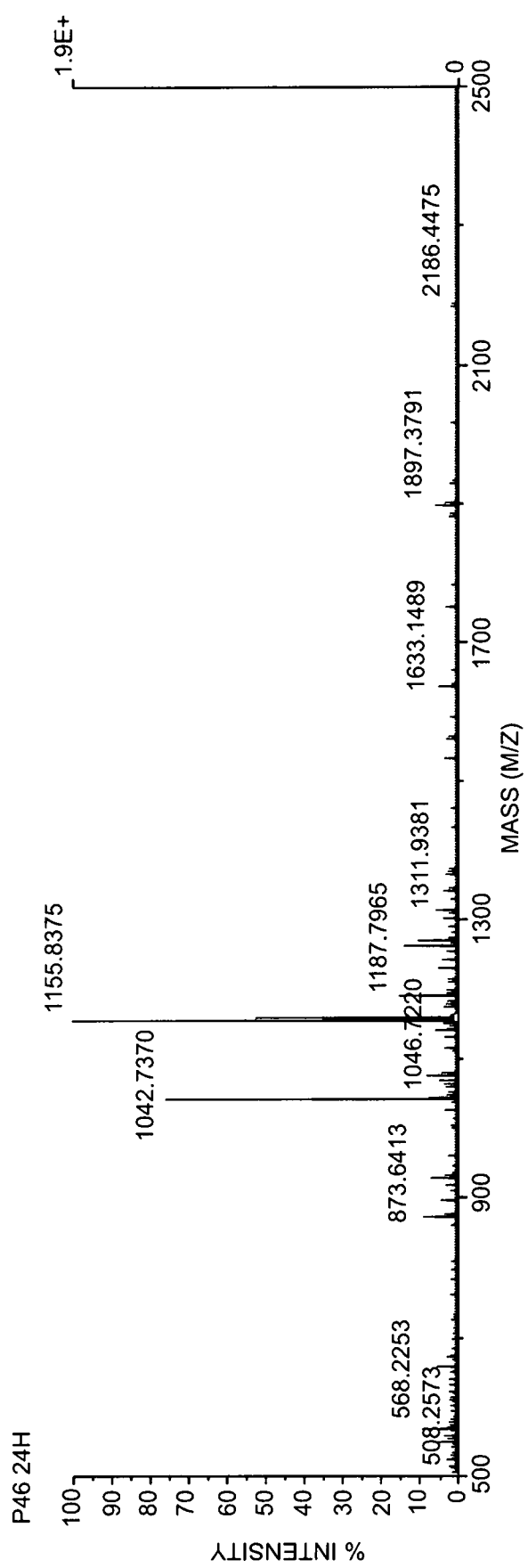

To determine the sensitivity of P46 to elastase digestion, P46 was synthesized and digested with elastase. The MS analysis results showed that P46 retained some sensitivity to elastase digestion (FIGS. 3A-3B). P46 was incubated with purified human neutrophil elastase at 1:100 enzyme:substrate molar ratio at 37° C. for 4 h (FIG. 3A) or 24 h (FIG. 3B). The elastase-generated smaller peptides were determined by MALDI-TOF analysis. Molecular weight of P46 is 1898.

CNP7 and CNP8 as Biologically Active, Neutrophil Elastase-Resistant Peptides Based on the amino acid sequence of P46 and enzymatic cleavage properties of elastase, we designed and synthesized five engineered peptides, -HIGKYGLRWRPKNSV (SEQ ID NO:11)-(NP7) and HIGKYGLRWRPKGSV (SEQ ID NO:12)-(NP8), HISKYILGWRPKNSV (SEQ ID NO:6) (NP9), HISKYILRGRPKNSV (SEQ ID NO:7) (NP10), HISKYILRWGPKNSV (SEQ ID NO:8) (NP11), and screened for resistance to elastase digestion. Of these, NP8 demonstrated the best biological activity on screening experiment of adult human dermal fibroblast survival in medium without serum but with 1 nM PDGF-BB after 6 days of incubation. NP9, NP10 and NP11 showed minimal biological activity in this screen.

Figure 4:
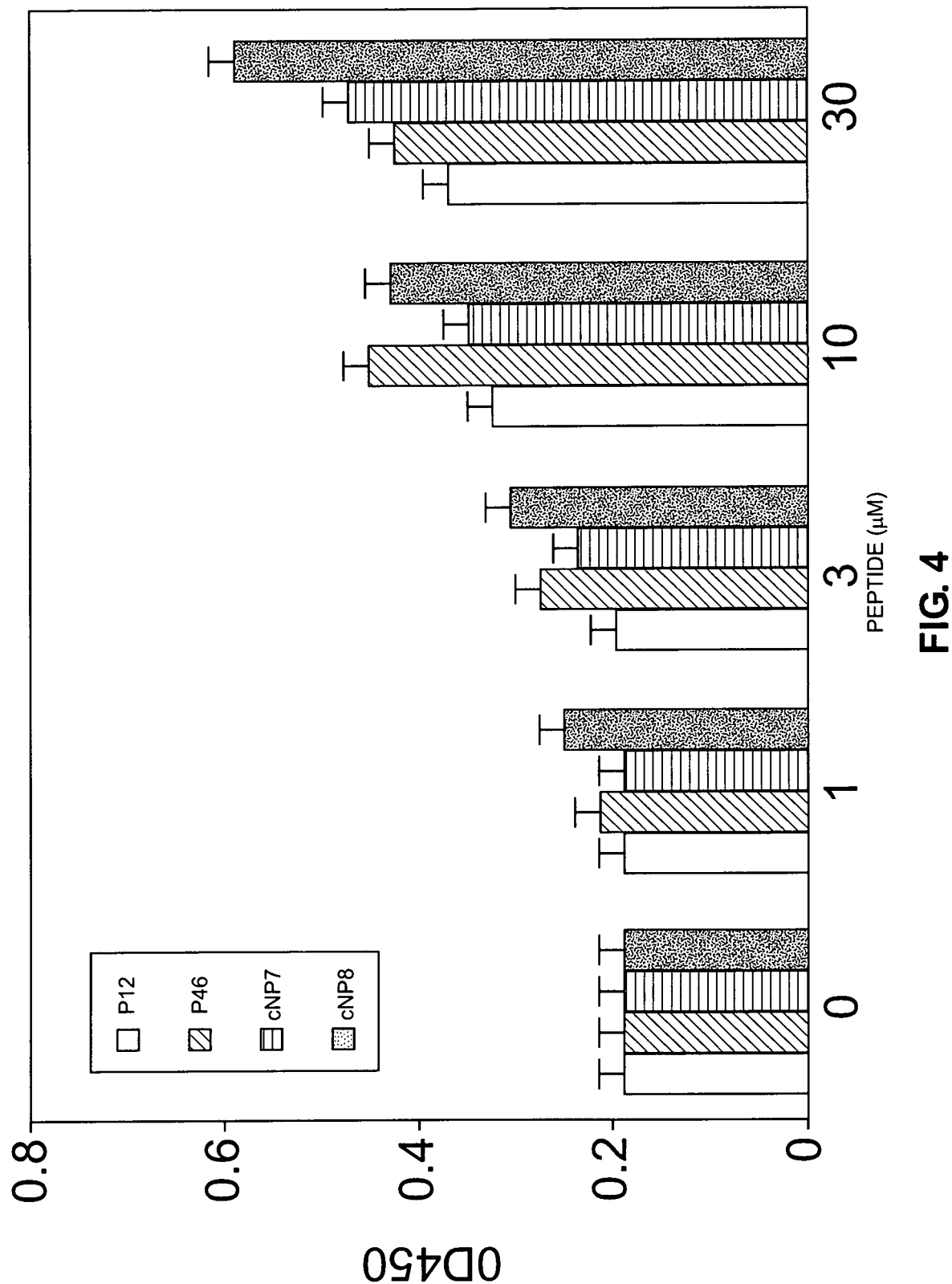
FIG. 4 shows bioactivity of P12, P46, cNP7 and cNP8. Adult human dermal fibroblasts, CF31, at 1000 cells/well were incubated at 37° C. in a collagen-coated 96-well plate with DMEM, 1 nM PDGF-BB with peptides at indicated doses for 6 days and then cell metabolism was measured by XTT assay, reading OD at 450 nm. Data represent the mean of 6 replicates.

P12, P46, cNP7 and cNP8 were compared for their ability to promote the survival of adult human dermal fibroblasts in the presence of PDGF-BB. Adult human dermal fibroblasts at 1000 cells/well were incubated in a collagen-coated 96-well plate with DMEM, 1 nM PDGF-BB with peptides at indicated doses for 6 days and then cell metabolism was measured by XTT assay. Data represent the mean of 6 replicates (FIG. 4). This bioactivity assay demonstrated all four peptides promoted the survival of adult human dermal fibroblasts and that cNP8 showed equivalent or better bioactivity, depending on the concentration, compared to P46 and cNP7.

Figure 5A:
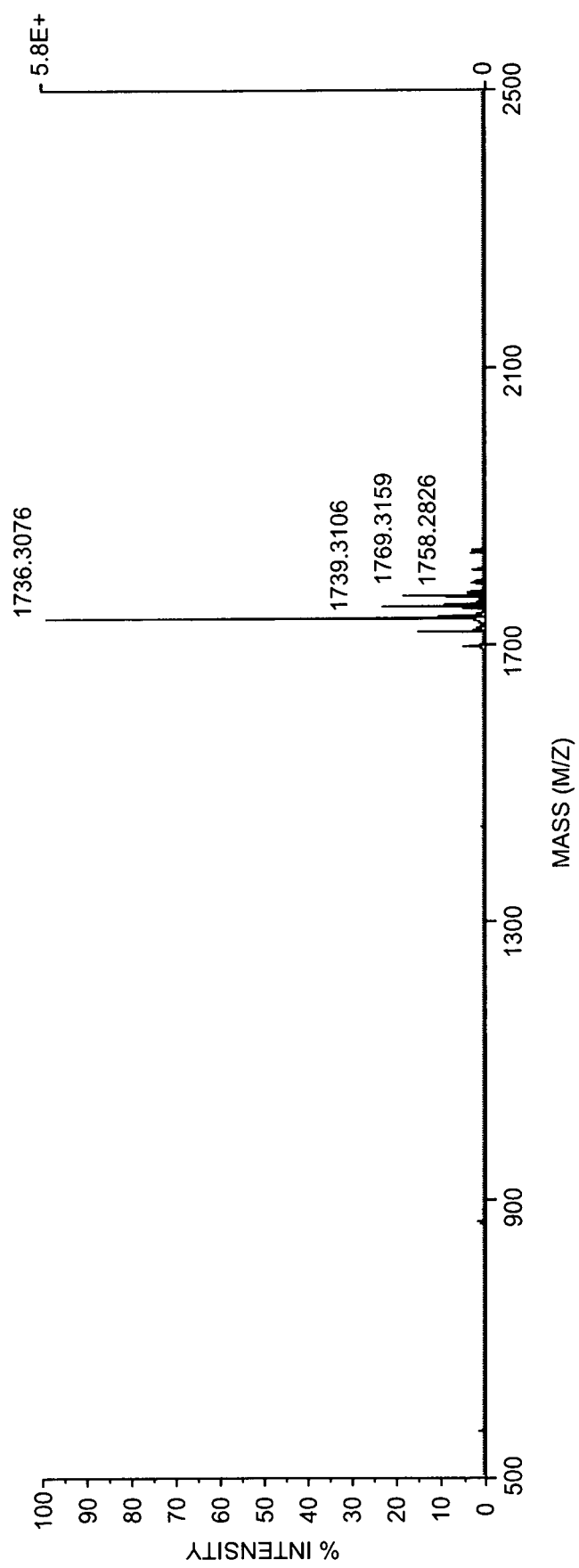
FIGS. 5A-5B show that cNP8, derived from P46, is resistant to digestion by neutrophil elastase. cNP8 was incubated with purified human neutrophil elastase at 1:100 enzyme:substrate molar ratio at 37° C. for 4 h (5A) or 24 h (5B). Peptides' stability was determined by MALDI-TOF analysis. Molecular weight of cNP8 is 1736. Intact peptide (MW=1736) was retained at 24 h.
Figure 5B:
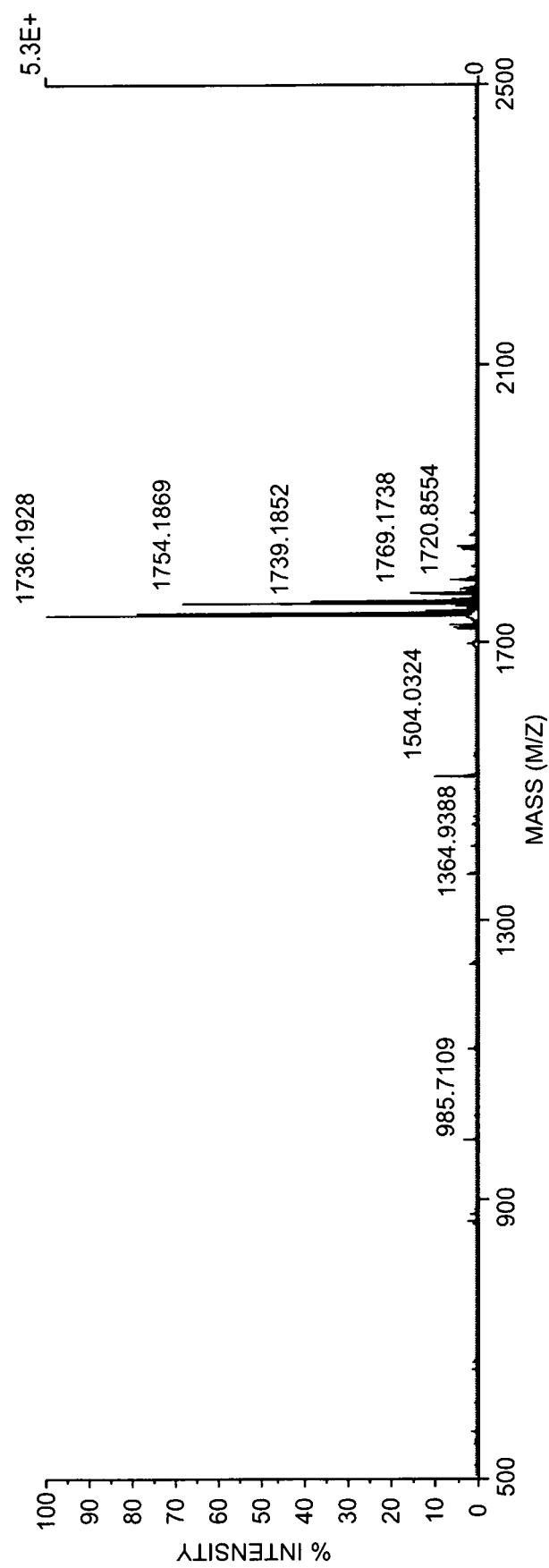

Results from peptide incubation with elastase showed that cNP8 was resistant to elastase digestion. cNP8, derived from P46, was incubated with purified human neutrophil elastase at 1:100 enzyme:substrate molar ratio at 37° C. for 4 h (FIG. 5A) or 24 h (FIG. 5B). Peptide's stability was determined by MALDI-TOF analysis. Molecular weight of cNP8 is 1736. A large majority of intact peptide was retained at 24 h. Thus, cNP8 is a peptide with both bioactivity and resistant to elastase digestion.

P46 and CNP8 Engineered from P46 have the Ability to Bind Growth Factors

Previous studies showed that fibronectin-derived bioactive peptide P12 interacts with platelet-derived growth factor-BB and enhances its activity to support fibroblasts survival. We showed, above, that both fibronectin-derived peptide P46 and elastase-resistant engineered peptide cNP8 demonstrated much higher bioactivity than that of P12. To study the binding activities of these peptides, real time interactions of P12, P46, and cNP8 with growth factors were determined by plasmon surface resonance (Biacore T200). The results demonstrated that both P46 and cNP8 showed similar binding activity as P12. They bind PDGF-BB and Transforming Growth Factor-Beta1 (TGF-β1), but did not bind to epidermal growth factor (EGF) and insulin-like growth factor-1 (IGF-1).

Surface Plasmon Resonance

In the Biacore2000 system, binding constants from kinetic data are determined by passing varying concentrations of FN peptides (analytes) over chip surfaces which are coupled with PDGF-BB (ligand), respectively. All kinetic experiments are carried out at 20° C. at a flow rate of 20 µl/min. For mass transport experiments, each analyte is injected at a fixed concentration and run at flow rates ranging from 5 to 75 µl/min. All analytes are injected over PDGF-BB ligand surfaces as well as over a control surface for 120 s, followed by 300 s of dissociation in running buffer. Regeneration of the sensor chip for subsequent injections is accomplished by pulse of 0.1% SDS. Mass transport experiments have detected little difference in response at different flow rates thus validating data from kinetic experiments. Sensorgrams are prepared and globally fitted using nonlinear least-squares analysis and numerical integration of the differential rate equations with the Biacore Bioevaluation software. Each sensorgram generated using a control surface is subtracted from the corresponding experimental sensorgrams, and the resulting curves are transformed to concentration units using the molecular mass of the injected species, the equivalence of 1000 resonance units (RU) per 1 ng/mm2, and a matrix thickness of 100 nm. Each data set, which consists of a series of sensorgrams from injections of different concentration of analyte over the same surface, is analyzed using kinetic models from Bioevaluation software.

Novel Peptides for Use in Wound Healing

Linear or cyclic peptides according to Formula I:

```
(I):
                                              (SEQ ID NO: 1)
H-X₁-X₂-K-Y-X₃-X₄-R-W-R-P-K-X₅-X₆-X₇
``` wherein $X_1$ is I or G or L,
$X_2$ is S or G,
$X_3$ is I or G or L,
$X_4$ is L or G,
$X_5$ is N or G,
$X_6$ is absent or S, and
$X_7$ is absent or V; and wherein no two consecutive amino acids in the first 13 amino acids of the polypeptide differ from the sequence HISKYILRWRPKN (SEQ ID NO:9), are useful for the treatment of wounds. These peptides promote the survival, migration or growth of human adult dermal fibroblasts and human adult cardiomyocytes, and are resistant to neutrophil elastase, an endopeptidase found in wound fluids.

Each linear or cyclic peptide selected from:

HISKYILRWRPKNSV, (SEQ ID NO: 10)

HISKYILRWRPKNS, (SEQ ID NO: 17)

HISKYILRWRPKN, (SEQ ID NO: 9)

HISKYILRWRPKGSV, (SEQ ID NO: 18)

HISKYILRWRPKGS, (SEQ ID NO: 19)

HISKYILRWRPKG, (SEQ ID NO: 20)

HGSKYILRWRPKNSV, (SEQ ID NO: 21)

HGSKYILRWRPKNS, (SEQ ID NO: 22)

HGSKYILRWRPKN, (SEQ ID NO: 23)

HGSKYILRWRPKGSV, (SEQ ID NO: 24)

HGSKYILRWRPKGS, (SEQ ID NO: 25)

HGSKYILRWRPKG, (SEQ ID NO: 26)

HLSKYILRWRPKNSV, (SEQ ID NO: 27)

HLSKYILRWRPKNS, (SEQ ID NO: 28)

HLSKYILRWRPKN, (SEQ ID NO: 29)

HLSKYILRWRPKGSV, (SEQ ID NO: 30)

HLSKYILRWRPKGS, (SEQ ID NO: 31)

HLSKYILRWRPKG, (SEQ ID NO: 32)

HIGKYILRWRPKNSV, (SEQ ID NO: 33)

HIGKYILRWRPKNS, (SEQ ID NO: 34)

HIGKYILRWRPKN, (SEQ ID NO: 35)

HIGKYILRWRPKGSV, (SEQ ID NO: 36)

HIGKYILRWRPKGS, (SEQ ID NO: 37)

HIGKYILRWRPKG, (SEQ ID NO: 38)

HISKYGLRWRPKNSV, (SEQ ID NO: 39)

HISKYGLRWRPKNS, (SEQ ID NO: 40)

HISKYGLRWRPKN, (SEQ ID NO: 41)

HISKYGLRWRPKGSV, (SEQ ID NO: 42)

HISKYGLRWRPKGS, (SEQ ID NO: 43)

HISKYGLRWRPKG, (SEQ ID NO: 44)

HGSKYGLRWRPKNSV, (SEQ ID NO: 13)

HGSKYGLRWRPKNS, (SEQ ID NO: 45)

HGSKYGLRWRPKN, (SEQ ID NO: 46)

HGSKYGLRWRPKGSV, (SEQ ID NO: 47)

HGSKYGLRWRPKGS, (SEQ ID NO: 48)

HGSKYGLRWRPKG, (SEQ ID NO: 49)

HLSKYGLRWRPKNSV, (SEQ ID NO: 50)

HLSKYGLRWRPKNS, (SEQ ID NO: 51)

HLSKYGLRWRPKN, (SEQ ID NO: 52)

HLSKYGLRWRPKGSV, (SEQ ID NO: 53)

HLSKYGLRWRPKGS, (SEQ ID NO: 54)

HLSKYGLRWRPKG, (SEQ ID NO: 55)

HIGKYGLRWRPKNSV, (SEQ ID NO: 11)

HIGKYGLRWRPKNS, (SEQ ID NO: 56)

HIGKYGLRWRPKN, (SEQ ID NO: 57)

HIGKYGLRWRPKGSV, (SEQ ID NO: 12)

HIGKYGLRWRPKGS, (SEQ ID NO: 58)

HIGKYGLRWRPKG, (SEQ ID NO: 59)

HISKYLLRWRPKNSV, (SEQ ID NO: 60)

HISKYLLRWRPKNS, (SEQ ID NO: 61)

HISKYLLRWRPKN, (SEQ ID NO: 62)

HISKYLLRWRPKGSV, (SEQ ID NO: 63)

HISKYLLRWRPKGS, (SEQ ID NO: 64)

HISKYLLRWRPKG, (SEQ ID NO: 65)

HGSKYLLRWRPKNSV, (SEQ ID NO: 66)

HGSKYLLRWRPKNS, (SEQ ID NO: 67)

HGSKYLLRWRPKN, (SEQ ID NO: 68)

HGSKYLLRWRPKGSV, (SEQ ID NO: 69)

HGSKYLLRWRPKGS, (SEQ ID NO: 70)

HGSKYLLRWRPKG, (SEQ ID NO: 71)

HLSKYLLRWRPKNSV, (SEQ ID NO: 72)

HLSKYLLRWRPKNS, (SEQ ID NO: 73)

HLSKYLLRWRPKN, (SEQ ID NO: 74)

HLSKYLLRWRPKGSV, (SEQ ID NO: 75)

HLSKYLLRWRPKGS, (SEQ ID NO: 76)

HLSKYLLRWRPKG, (SEQ ID NO: 77)

HIGKYLLRWRPKNSV, (SEQ ID NO: 78)

HIGKYLLRWRPKNS, (SEQ ID NO: 79)

HIGKYLLRWRPKN, (SEQ ID NO: 80)

HIGKYLLRWRPKGSV, (SEQ ID NO: 81)

HIGKYLLRWRPKGS, (SEQ ID NO: 82)

HIGKYLLRWRPKG, (SEQ ID NO: 83)

HISKYIGRWRPKNSV, (SEQ ID NO: 84)

HISKYIGRWRPKNS, (SEQ ID NO: 85)

HISKYIGRWRPKN, (SEQ ID NO: 86)

HISKYIGRWRPKGSV, (SEQ ID NO: 87)

HISKYIGRWRPKGS, (SEQ ID NO: 88)

HISKYIGRWRPKG, (SEQ ID NO: 89)

HGSKYIGRWRPKNSV, (SEQ ID NO: 15)

HGSKYIGRWRPKN, (SEQ ID NO: 90)

HGSKYIGRWRPKN, (SEQ ID NO: 91)

HGSKYIGRWRPKGSV, (SEQ ID NO: 16)

HGSKYIGRWRPKGS, (SEQ ID NO: 92)

HGSKYIGRWRPKG, (SEQ ID NO: 93)

HLSKYIGRWRPKNSV, (SEQ ID NO: 94)

HLSKYIGRWRPKNS, (SEQ ID NO: 95)

HLSKYIGRWRPKN, (SEQ ID NO: 96)

HLSKYIGRWRPKGSV, (SEQ ID NO: 97)

HLSKYIGRWRPKGS, (SEQ ID NO: 98)

HLSKYIGRWRPKG, (SEQ ID NO: 99)

HIGKYIGRWRPKNSV, (SEQ ID NO: 14)

HIGKYIGRWRPKNS, (SEQ ID NO: 100)

HIGKYIGRWRPKN, (SEQ ID NO: 101)

HIGKYIGRWRPKGSV, (SEQ ID NO: 102)

HIGKYIGRWRPKGS (SEQ ID NO: 103)

or

HIGKYIGRWRPKG (SEQ ID NO: 104)

promotes the survival, migration or growth of human adult dermal fibroblasts and/or human adult cardiomyocytes, is resistant to neutrophil elastase and is useful for the treatment of wounds and/or cardiovascular disease.

In a particular embodiment, each linear or cyclic peptide: HISKYILRWRPKNSV (SEQ ID NO:10) (P46), HIGKYGLRWRPKNSV (SEQ ID NO:11) (NP7), HIGKYGLRWRPKGSV (SEQ ID NO:12) (NP8), HGSKYGLRWRPKNSV (SEQ ID NO:13), HIGKYIGRWRPKNSV (SEQ ID NO:14), HGSKYIGRWRPKNSV (SEQ ID NO:15) or HGSKYIGRWRPKGSV (SEQ ID NO:16) promotes the survival, migration or growth of human adult dermal fibroblasts and/or human adult cardiomyocytes, is resistant to neutrophil elastase and is useful for the treatment of wounds and/or cardiovascular disease.

In another particular embodiment, cyclic HIGKYGLRWRPKGSV (SEQ ID NO:12) (NP8) promotes the survival, migration or growth of human adult dermal fibroblasts and/or human adult cardiomyocytes, is resistant to neutrophil elastase and is useful for the treatment of wounds and/or cardiovascular disease.

All peptides described herein are presented in a linear format of standard, single-letter amino acid codes, reading from the N terminus on the left to the C terminus on the right. "Cyclic" or "cyclized" peptides may be represented in linear form but have the N terminus amino acid bound to the C terminus amino acid by one or more standard methods, described below.

A biologically active fibronectin fragment or variant of a FN fragment described herein is one that functions as a PDGF-BB binding peptide, is resistant to human neutrophil elastase, and functions to a useful extent and in substantially the same manner as the corresponding FN fragment. For example, where a FN fragment having a naturally occurring sequence binds a GF with a particular affinity and, upon administration to a patient, effectively enhances or alters the GF activity to at a site where the GF is needed, a biologically active variant of that FN fragment will be one that, although not identical to the FN fragment, will bind the same GF(s) with sufficiently useful affinity and similarly enhances or alters the GF(s) at a site of need. For ease of reading, we do not repeat the term "or a biologically active variant thereof" after every reference to a FN fragment or other protein or peptide. It is to be understood that where FN fragments having a naturally occurring sequence are useful, so are biologically active variants of those fragments.

With respect to function, a fragment can bind a polypeptide growth factor with an affinity of at least or about $1 \times 10^{-7}$M (e.g., at least $1 \times 10^{-8}$M; $1 \times 10^{-9}$ M; or more). Alternatively, or in addition, a fragment may support FN-null cell survival and/or proliferation.

Alternatively, or in addition, the fragment can further include a substituent at the amino-terminus or carboxy-terminus. The substituent can be an acyl group or a substituted or un-substituted amine group (e.g., the substituent at the N-terminus can be an acyl group and the C-terminus can be amidated with a substituted or un-substituted amine group (e.g., an amino group having one, two, or three substituents, which may be the same or different)). The amine group can be a lower alkyl (e.g., an alkyl having 1-4 carbons). The acyl group can be a lower acyl group (e.g., an acyl group having up to four carbon atoms), especially an acetyl group.

The fragments of fibronectin, including the modified fragments described above, can be protease resistant and can include one or more types of protecting groups such as an acyl group, an amide group, a benzyl or benzoyl group, or a polyethylene glycol. More specifically, a fragment of fibronectin, including the modified fragments described above, can be N-terminally acetylated and/or C-terminally amidated.

The fragments of fibronectin can also be modified in order to improve absorption, including for example, an addition of sugar residues to enhance transport across the blood-brain barrier.

Any of the fragments can include at least one amino acid residue in the D-form.

Any of the fragments can include at least one non-naturally occurring or modified amino acid residue (e.g., 4-hydroxyproline, gamma-carboxyglutamic acid, o-phosphoserine, o-phosphotyrosine, or delta-hydroxylysine). Non-naturally occurring amino acid residues are amino acid residues other than the 20 naturally occurring, genetically encoded amino acids. Other examples include naphthylalanine, which can be substituted for tryptophan to facilitate synthesis, L-hydroxypropyl, L-3,4-dihydroxyphenylalanyl, alpha-amino acids such as L-alpha-hydroxylysyl and D-alpha-methylalanyl, L-alpha-methylalanyl, beta-amino acids, and isoquinolyl. Fragments having non-naturally occurring amino acid residues may be referred to as synthetic fragments and constitute one type of variant as described herein. Other variants include fragments of fibronectin in which a naturally occurring side chain of an amino acid residue is replaced with a non-naturally occurring side chain (in either the L- or D-form). In another aspect, the invention features polypeptides that include a sequence that is reversed with respect to the N- and C-termini of a sequence naturally found in a fibronectin polypeptide or a biologically active variant thereof.

Any of the fragments in the present compositions can be one of a plurality of fragments present. These fragments may be linked together by methods described herein. As noted, fragments of fibronectin, including the variant forms described herein, can further include a heterologous polypeptide (i.e., a polypeptide having a sequence that does not appear in a fibronectin). The heterologous polypeptide can be a polypeptide that increases the circulating half-life, cell penetration or transdermal penetration of the fragment to which it is attached.

The fragments can be contained within physiologically acceptable compositions, or they may be contained within compositions that are not suitable for administration to a living being (e.g., concentrated stocks or frozen or lyophilized compositions).

The physiologically acceptable compositions can be pharmaceutical compositions, and methods of treating patients are described further below. The physiologically acceptable compositions can also be non-pharmaceutical compositions or pharmaceutical compositions that can be dispensed without a physician's prescription. For example, they can be sold to a distributer or "over the counter" for cosmetic purposes (e.g., to reduce the risk of damage from the skin or to minimize or repair damage to the skin). For example, the fragments of fibronectin and compositions that include them or combinations of them (e.g., a FN-growth factor complex) can be incorporated in topical formulations sold as cosmetics, moisturizers and the like, sunscreens, shampoos or conditioners, soaps or other foaming cleansers, or lip balm.

The invention also encompasses nucleic acid molecules that encode the polypeptides described herein. Specific nucleic acid molecules, vectors (e.g., plasmid vectors or viral vectors), and host cells containing them are described further below, as are physiologically acceptable compositions containing them.

Other compositions of the present invention are tissue engineered products that include a fragment of a fibronectin or a biologically active variant thereof. As in other compositions, the fragment or the variant thereof can bind a polypeptide growth factor or enhance growth factor activity (as described above and further below), which factor may subsequently retain biological activity and may be administered to a patient.

Other compositions of the present invention comprise a solid support that is associated with (e.g., bound to or impregnated with) one or more of the fragments of fibronectin, or the biologically active variants thereof, described herein. The support can be, for example, a tissue culture vessel (e.g., a plate or flask) or device (e.g., a medical device such as one used in wound dressing (e.g., a bandage or gauze), wound repair (e.g., a suture or "steri-strip"), surgical repair (e.g., a surgical mesh), or a tissue implant (e.g. a stent). The fragment of fibronectin, or the biologically active variant thereof, can be bound to an active growth factor, including any of those described above.

The methods of the invention include methods for promoting wound healing. These methods include a step of administering to a patient a therapeutically effective amount of a pharmaceutical composition comprising a fragment of fibronectin, or a biologically active variant thereof, as described herein. The fragment of fibronectin, or the biologically active variant thereof, can be present in a complex with one or more growth factors. The methods can optionally include a step of identifying a patient in need of treatment. Such patients include patients who are suffering from a surgical extirpation or incision of the skin, mucosa, underlying connective tissue, fascia, ligament, tendon, cartilage, bone, nerve or muscle; patients who are suffering from a traumatic laceration or tissue loss of the skin, mucosa, underlying connective tissue, fascia, nerve or muscle; and patients who are suffering from a thermal burn, chemical burn, or ulceration of the skin, mucosa, underlying connective tissue, fascia, nerve or muscle.

As used herein, a "burn" is tissue damage due to exposure to heat or a caustic chemical. A "thermal burn" is tissue damage due to exposure to heat. A "chemical burn" is tissue damage due to exposure to a caustic chemical, often strong alkali or strong acid. Agents of chemical burns to be treated by the peptides defined by the invention include, but are not limited to, phenol, creosol, mustard gas, phosphorus, nitrogen mustard, arsenic compounds, ammonia, caustic potash, lime, sodium hydroxide, hydrochloric acid, and sulphuric acid.

The methods of the invention include methods for treating cardiovascular disease, including decreasing blood vessel occlusion from aggregates of red blood cell and/or fibrinogen and/or fibrin, as can occur in burn wounds; myocardial infarction; multi-organ failure; diabetes; sickle cell anemia; polycythemia vera; and hyperfibrinogenemia. These methods include a step of administering to a patient a therapeutically effective amount of a pharmaceutical composition comprising a fragment of fibronectin, or a biologically active variant thereof, as described herein. The fragment of fibronectin, or the biologically active variant thereof, can be present in a complex with one or more growth factors. The methods can optionally include a step of identifying a patient in need of treatment.

Suitable formulations are described further below and, generally, take the form of a solution, lotion, ointment, gel, cream or salve. The fragments of fibronectin, whether or not complexed with a growth factor, can also be administered by way of their inclusion in an extracellular matrix (ECM; e.g., a natural or engineered ECM), a bandage, dressing, compress, or the like.

By other methods of the invention, one can localize an endogenous growth factor to a tissue of a patient. These methods can be carried out by administering, to the patient, a therapeutically effective amount of a composition that includes a fragment of fibronectin, or a biologically active variant thereof, as described herein. As in the more specific treatment methods described above, these compositions can be administered by way of topical application of a pharmaceutical composition, an engineered ECM, or a solid support. These methods can be described as methods of delivering one or more growth factors to a patient. The methods can optionally include a step of identifying a patient in need of treatment. Such patients include patients who are suffering from an injury to a tissue, a loss of a tissue or a disorder resulting in tissue disfigurement or dysfunction. More specifically, the patient can be suffering from an injury or loss to the brain, spinal cord or nerves or a disorder resulting in brain, spinal cord or nerve dysfunction; an injury or loss to the heart or blood vessels or a disorder resulting in heart or blood vessel dysfunction; an injury or loss to the lung, nasopharyngeal tract, sinuses, trachea or airways or a disorder resulting in lung, nasopharyngeal tract, sinus, trachea or airway dysfunction; an injury or loss to the gastrointestinal tract, liver or pancreas or a disorder resulting in gastrointestinal tract, liver or pancreas dysfunction; an injury or loss to a kidney, ureters, bladder or urethra or a disorder resulting in kidney, ureter, bladder or urethra dysfunction; an injury or loss to bone, cartilage, synovium, meniscus, ligament, tendon or nucleus pulposus or a disorder resulting in bone, cartilage, synovium, meniscus, ligament, tendon or nucleus pulposus dysfunction; an injury or loss to lips, tongue or gums or a disorder resulting in lip, tongue or gum dysfunction; an injury or loss to the subcutaneous tissue or a disorder resulting in subcutaneous tissue dysfunction.

The invention can also be described in terms of "use," in which case it encompasses "use" of the compositions described herein, including FN fragments, peptide derivatives of FN fragments, complexes containing one or more of FN fragments and/or peptide derivatives of FN fragments, including those with a bound GF, nucleic acids encoding the present FN fragments and/or peptide derivatives of FN fragments, expression vectors, host cells, and tissue engineered products, including those that contain biomaterials, for promoting tissue regeneration and/or tissue repair. For example, the present compositions can be used in promoting wound healing, or for the preparation of a medicament for the promotion of tissue regeneration or wound healing. The tissue regeneration or repair may result in healing with little or no scarring, in contradistinction with usual adult wound healing.

As used herein, "growth factor binding peptide" (or "GFBP") and "growth factor enhancing peptide" (or "GFEP") are used synonymously.

As used herein, "cosmetic treatment" refers to the use of a physiologically acceptable composition to improve or maintain the appearance of an individual.

As detailed above, we have found, inter alia, that specific fragments of fibronectin and peptides derived from fibronectin can bind various growth factors (e.g., IGF-1, HGF, TGF-β1, TGF-β2, bFGF, FGF-7, PDGF-BB, VEGF-A, or NGF), and the bound growth factors can retain or show enhanced/decreased biological activity. The present invention features compositions that include such fragments and peptides, with or without bound growth factors in the represented families (i.e., in the IGF, TGF, FGF, PDGF, VEGF, and NGF families), in various formulations and configurations. The fragments and peptides may promote synergy with GFs to which the FN fragments or peptides do not bind. In one configuration, the FN fragments or peptides, or FN fragment or peptide/GF-containing complexes can be incorporated into engineered two- or three-dimensional extracellular matrices (which we may abbreviate herein as engECM or refer to as synthetic matrices), and these can include any of, or any combination of, the peptides described herein (e.g., a peptide conforming to Formulas I) or biologically active variants thereof. The growth factor(s) incorporated can be, for example, IGF-1, TGF-β1, TGF-β2, bFGF, FGF-7, PDGF-BB, VEGF-A, or NGF; any combination or sub-combination thereof; or another specific growth factor in the same family as those listed. The growth factors can be exogenously added to the peptide-containing formulation (e.g., a FN fragment-containing matrix), or the formulation (e.g., the matrix) can be generated without growth factors. In the latter case, when placed in the vicinity of an endogenous supply of growth factors, the growth factors can be recruited by the matrix. The matrix can also recruit cells and induce them to differentiate, produce tissue or proliferate (presumably by virtue of the inclusion or recruitment of growth factors, although the invention is not limited to compositions that function by any particular mechanism).

The matrix can include any type of biomaterial (e.g., a biopolymer). For example, the matrix can be or can include a hydrogel (e.g., an intramolecularly crosslinked hydrogel). The present peptides and GFs can be incorporated in or associated with many different types of materials (e.g., hyaluronan). The matrix can have, for example, a polycarbonate backbone, or include biodegradable polyurethanes. Further examples of suitable biopolymers are: proteins (e.g., collagen), protein-containing macromolecules (e.g., proteoglycans), silk (e.g., a derivatized silk), alginate, chitan and chitosan.

For preparation of pharmaceutical compositions containing one or more of the present peptides, for prophylactic and/or therapeutic treatments, the active ingredients (e.g., the peptide alone or the peptide bound to GF(s)) can be incorporated alone or in combination with other active agents into compositions suitable for administration to a patient. The formulations can be made using methods routine in the art and particular guidance may be provided by prior formulations of protein-based therapeutics. The compositions will be physiologically acceptable (i.e., substantially non-toxic) and may be formulated as prescription medications or over-the-counter products. Pharmaceuticals or pharmaceutically acceptable compositions contain compounds (e.g., polypeptides), other materials (e.g., diluents), and/or dosage forms that are, within the scope of sound medical judgment, suitable for use in contact with the tissues of human beings and animals without excessive toxicity, irritation, allergic response, or other problem or complication, commensurate with a reasonable benefit/risk ratio.

Nucleic acid molecules that encode the peptides described herein can also be formulated for use in cell culture or administration to a patient or subject. Such compositions commonly include a pharmaceutically acceptable carrier, and carriers are contemplated in the present formulations. Any conventional media or agent compatible with the active ingredients can be used in the present compositions. While formulations and methods of use are described further below, we note here that application to human patients is intended, as is application to animals (e.g., domesticated, farm, or show animals). The invention extends to non-physiologically acceptable compositions in that it extends to preparatory compositions and compositions suitable for storage (e.g., concentrated stocks and frozen or lyophilized preparations).

The specific sequences described herein are derived from human plasma fibronectin. In addition, one can use corresponding sequences (e.g., fragments having a corresponding sequence from any fibronectin isoform of any species).

With respect to function, the featured peptides can bind a polypeptide growth factor, for example PDGF-BB, with an affinity of about or at least about $1\times10^{-6}$-$1\times10^{-7}$ (e.g., about or at least about $5\times10^{-7}$; $1\times10^{-8}$; $5\times10^{-8}$; $1\times10^{-9}$; or $5\times10^{-9}$). Alternatively or in addition, the peptides support FN-null cell survival and/or proliferation secondary to intrinsic growth factor activity and/or growth factor enhancing activity.

Although applicants do not wish to be bound by theory, the peptides described herein are useful in the treatment of skin-aging or photo-aging (e.g., for the treatment of wrinkles) and in other cosmetic treatments in that certain fragments derived from fibronectin have been shown to promote fibroblast survival and proliferation. Furthermore, the peptides described herein may be used to deliver growth factors that promote fibroblast survival and proliferation to sites needing cosmetic treatment. For example, peptides may be incorporated into transdermal patches or any other device to facilitate their delivery with or without growth factors.

Although applicants do not wish to be bound by theory, the peptides described herein are useful in the treatment of wounds insofar as they stimulate fibroblast survival, proliferation and/or migration. Additionally, the peptides described herein are useful, for example, as components of growth factor delivery devices such as engineered three-dimensional extracellular matrices.

Modifications of Peptides

The featured fragments and biologically active variants thereof can be modified in numerous ways. For example, agents, including additional amino acid residues, other substituents, and protecting groups can be added to either the amino terminus, the carboxy terminus, or both. The modification can be made for the purpose of altering the fragments' form or altering the way the fragments bind to or interact with one another, with non-identical fragments, or with other polypeptides. While the peptides of the present invention may be linear or cyclic, cyclic peptides generally have an advantage over linear peptides in that their cyclic structure is more rigid and hence their biological activity may be higher than that of the corresponding linear peptide (see, generally, Camarero and Muir, J. Am. Chem. Soc. 121:5597-5598, 1999).

Strategies for the preparation of circular polypeptides from linear precursors have been described and can be employed with the present fragments. For example, a chemical cross-linking approach can be used to prepare a backbone cyclized version of the peptide (Goldenburg and Creighton, J. Mol. Biol., 165:407-413, 1983). Other approaches include chemical intramolecular ligation methods (see, e.g., Camarero et al., Angew. Chem. hit. Ed., 37:347-349, 1998; Tam and Lu, Prot. Sci., 7:1583-1592, 1998; Camarero and Muir, Chem. Commun., 1997:1369-1370, 1997; and Zhang and Tam, J. Am. Chem. Soc. 119:2363-2370, 1997) and enzymatic intramolecular ligation methods (Jackson et al., J. Am. Chem. Soc., 117:819-820, 1995), which allow linear synthetic peptides to be efficiently cyclized under aqueous conditions. See also U.S. Pat. No. 7,105,341.

Alternatively, or in addition, any of the present fragments can further include one or more substituents. For example, the fragment can include a substituent at the amino-terminus, carboxy-terminus, and/or on a reactive amino acid residue side-chain. The substituent can be an acyl group or a substituted or unsubstituted amine group (e.g., the substituent at the N-terminus can be an acyl group and the C-terminus can be amidated with a substituted or unsubstituted amine group (e.g., an amino group having one, two, or three substituents, which may be the same or different)). The amine group can be a lower alkyl (e.g., an alkyl having 1-4 carbons), alkenyl, alkynyl, or haloalkyl group. The acyl group can be a lower acyl group (e.g., an acyl group having up to four carbon atoms), especially an acetyl group. The substituent can be a non-protein polymer, for example, a polyether, a polyethylene glycol (PEG), a polypropylene glycol, or a polyoxyalkylene, a polyalkylene glycol (for example, polypropylene glycol (PPG), a polybutylene glycol (PBG), or a PPG-PEG block/random polymer. The peptide can be modified by a non-protein polymer by methods known in the art and in the manner set forth in U.S. Pat. Nos. 4,640,835; 4,496,689; 4,301,144; 4,670,417; 4,791,192 or 4,179,337. The modification (e.g., PEGylation) can stabilize the peptide, reduce its antigenicity, decrease the required dosage, and/or augment its targeting ability.

The non-protein polymer can vary in size and shape. For example, any of the non-protein polymers listed above (e.g., PEG) can be linear, branched, or comb-shaped. Regarding size, the molecular weight can vary. For example, the PEG can have a molecular weight of, for example, about 300 kDa, about 1,000 kDa, about 2,000 kDa, about 3,000 kDa, about 4,000 kDa, about 5,000 kDa, about 6,000 kDa, about 7,000 kDa, about 8,000 kDa, about 9,000 kDa, about 10,000 kDa, about 11,000 kDa, about 12,000 kDa about 13,000 kDa about 14,000 kDa about 15,000 kDa, about 20,000 kDa, about 30,000 kDa, about 40,000 kDa, or about 50,000 kDa. For example, the PEG can be of a molecular weight anywhere in between 300 kDA and 2000 kDA, 300 kDA and 3000 kDA, 1000 kDA and 2000 kDA and 1000 and 3000 kDA.

The non-protein polymer (e.g., PEG) can be linked to the fragment by any number of functional group chemistries (e.g., carboxylated-mPEGs, p-nitrophenyl-PEGs, aldehyde-PEGs, amino-PEGs, thiol-PEGs, maleimide-PEGs, aminoxy-PEGs, hydrazine-PEGs, tosyl-PEGS, iodoacetamide-PEGs, succinimidylsuccinate-PEGs, succinimidylglutarate-PEGS, succinimidylcarboxypentyl-PEGs, p-nitrophen0 ycarbonate-PEGs, or ethanethiol-PEGs). The non-protein polymer (e.g., PEG) can be linked to the fragment through any number of chemical groups including, but not limited to, amino-terminal amino acids, carboxy-terminal amino acids, free amines, and free sulfhydryl groups.

The non-protein polymer (e.g., PEG) may be a functionalized (for example, a monofunctional activated linear PEG, a homobifunctional activated linear PEG, a heterobifunctional activated linear PEG, a multiarmed activated PEG (e.g., 2-armed, 4-armed, 8-armed, etc.), a branched activated PEG and a comb-shaped activated PEG).

As used herein, the term "alkyl" is meant to refer to a saturated hydrocarbon group, which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms.

As used herein, "alkenyl" refers to an alkyl group having one or more double carbon-carbon bonds. Example alkenyl groups include ethenyl, propenyl, and the like. "Alkynyl" refers to an alkyl group having one or more triple carbon-carbon bonds. Example alkynyl groups include ethynyl, propynyl, and the like. "Haloalkyl" refers to an alkyl group having one or more halogen substituents. Example haloalkyl groups include CF3, C2F5, CHF2, CCl3, CHCl2, C2Cl5, and the like.

As used herein, "polyether" refers to a polymer containing ether linkages. Examples include polyethylene glycol.

The fragments, including the modified fragments described above, can be protease resistant and can include one or more types of protecting groups such as an acyl group, an amide group, a benzyl or benzoyl group, or a polyethylene glycol. More specifically, a fragment, including the modified fragments described above, can be N-terminally acetylated and/or C-terminally amidated.

Where non-naturally occurring or modified amino acid residues are included they can be selected from the following or many others available in the art: 4-hydroxyproline, gamma-carboxyglutamic acid, o-phosphoserine, o-phosphotyrosine, or delta-hydroxylysine. Other examples include naphthylalanine, which can be substituted for tryptophan to facilitate synthesis, L-hydroxypropyl, L-3,4-dihydroxyphenylalanyl, alpha-amino acids such as L-alpha-hydroxylysyl and D-alpha-methylalanyl, L-alpha-methylalanyl, beta-amino acids, and isoquinolyl. Fragments having non-naturally occurring amino acid residues may be referred to as synthetic fragments and constitute one type of variant as described herein. Other variants include fragments in which a naturally occurring side chain of an amino acid residue (in either the L- or D-form) is replaced with a non-naturally occurring side chain.

In one embodiment, the fragments can have three extra amino acids (MetGlySer) at either terminus (or both) (e.g., at the N-terminus) and seven to eight extra amino acids (ThrSerHisHisHisHisHisHisCys) (SEQ ID NO:105) at either terminus (or both) (e.g., at the C-terminus).

For guidance on fragment modification by reduction/alkylation and/or acylation, one can consult Tarr, Methods of Protein Microcharacterization, J. E. Silver ed., Humana Press, Clifton N.J. 155-194, 1986; for guidance on chemical coupling to an appropriate carrier, one can consult Mishell and Shiigi, eds, Selected Methods in Cellular Immunology, W H Freeman, San Francisco, Calif. (1980) and U.S. Pat. No. 4,939,239; and for guidance on mild formalin treatment, one can consult Marsh, Int. Arch. of Allergy and Appl. Immunol., 41:199-215, 1971.

Any of the peptides in the featured compositions can be one of a plurality present in a multimeric form (e.g., a dimer). These multimers can be linear or branched. The multimeric form can also include one or more types of fragments and a backbone structure. Where two or more fragments are present, they may be identical or non-identical. A smaller structure, referred to as a linker, may also be present and may mediate attachment of the fragments to the backbone. Generally, the linker is smaller than the backbone. The nature of the backbone structure is not critical, and many different types of molecules may be used. One example of a linker structure is an oligolysine molecule having, for example, two or more lysine residues (e.g., 2, 3, 4, or more lysine residues). Two or more fragments of the invention (e.g., two three or four polypeptides) may be attached to lysine residues by, for example, peptide bonds. These fragments, having a polylysine linker, can be linked to a backbone structure. For example, the invention encompasses:

```
                                    (SEQ ID NO: 106)
    Backbone-KKK HIGKYGLRWRPKGSV
    and
                                    (SEQ ID NO: 107)
    HIGKYGLRWRPKGSVKKK-Backbone.
```

A backbone structure, for example, an oligolysine molecule, may be linear or branched. A multimeric peptide of the invention on a branched backbone molecule may be referred to herein as a "dendrimeric" peptide.

Any of the fragments described herein, including the variant forms described herein, can further include a heterologous polypeptide (i.e., a polypeptide having a sequence that does not appear in a fibronectin). The heterologous polypeptide can be a polypeptide that increases the circulating half-life of the fragment to which it is attached (e.g., fused, as in a fusion protein). The heterologous polypeptide can be an albumin (e.g., a human serum albumin or a portion thereof) or a portion of an immunoglobulin (e.g., the Fc region of an IgG).

Polypeptide growth factors that can be bound by the FN described herein can be within the insulin-like growth factor (IGF) family (e.g., IGF-1), within the transforming growth factor (TGF) family (e.g., TGF-β1 or TGF-β2), within the fibroblast growth factor (FGF) family (e.g., bFGF or FGF-7), within the platelet-derived growth factor (PDGF) family (e.g., PDGF-BB), within the vascular endothelial growth factor (VEGF) subfamily (e.g., VEGF-A), or within the nerve growth factor (NGF) family. To determine whether fibronectin fragments bind growth factors that have retained a biological activity, standard biological assays can be carried out. For example, as outlined in the Examples below, migratory responses to bound growth factors that usually stimulate migration can be carried out. For example, one can compare the effect of a bound and unbound growth factor on fibroblast migration or granulation tissue formation. Specifically, if a growth factor is a PDGF (e.g., PDGF-BB), migration of AHDF cells can be analyzed.

Compounds mimicking the necessary conformation of the fibronectin fragments described herein are contemplated as within the scope of this invention. A variety of designs for such mimetics are possible. U.S. Pat. Nos. 5,192,746; 5,169, 862; 5,539,085; 5,576,423; 5,051,448; and 5,559,103, all hereby incorporated by reference, describe multiple methods for creating such compounds.

Physiologically Acceptable Compositions

A present pharmaceutical composition is formulated to be compatible with its intended route of administration, for example, oral or parenteral (e.g., intravenous, intradermal, subcutaneous, intraperitoneal, intramuscular, by inhalation, transdermal (topical), and transmucosal administration). Given the ability of the present FN fragments, and GF-containing complexes bearing these fragments, to facilitate wound healing, topical formulations are particularly envisioned.

Solutions or suspensions used for parenteral administration can include: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The composition can be aliquoted or packaged in ampules, disposable syringes, single or multiple dose vials made of glass or plastic, bottles, and the like, and such packaged forms, along with instructions for use, are within the scope of the present invention. Preferably, the compositions are sterile at a medically acceptable level in view of the intended route of administration.

Pharmaceutical compositions adapted for injection include, for example, sterile aqueous solutions (where water soluble) or dispersions and sterile powders for the extemporaneous preparation of sterile injectable solutions or dispersion. For intravenous administration, suitable carriers include, for example, physiological saline, bacteriostatic water, Cremophor EL™ (BASF, Parsippany, N.J.) and phosphate buffered saline (PBS). In all cases, the compositions prepared for administration should be sterile and should be fluid or convertible to a fluid at least sufficient for easy syringability. The composition and/or nucleic acid constructs should be stable under the conditions of manufacture and storage and should be preserved against the contaminating action of microorganisms such as bacteria and fungi. Preservatives against microorganisms can include various antibacterial and antifungal agents, for example, parabens, chlorobutanol, phenol, ascorbic acid, thimerosal, and the like.

The carrier can be a solvent or dispersion medium containing, for example, water, ethanol, polyol (for example, glycerol, propylene glycol, and liquid polyethylene glycol, and the like), and suitable mixtures thereof. Fluidity can be maintained, for example, by the use of a coating such as lecithin, by the maintenance of the required particle size in the case of dispersions and by the use of surfactants.

In many cases, it will be desirable for the composition to be isotonic to blood. This can be accomplished using various isotonic agents, for example, sugars, polyalcohols such as manitol, sorbitol, sodium chloride in the composition.

Delayed or extended absorption of the injectable compositions can be desirable and can be achieved by including in the composition an agent which delays absorption, for example, aluminum monostearate and gelatin, or by coating micro- or nano-particles of active agent in the composition with materials that delayed or extended release of components.

Sterile injectable solutions can be prepared, for example, by solubilizing or suspending the active compound in the required amount in an appropriate solvent with one or a combination of additional ingredients. Typically creation of such solution or suspension is followed by sterile filtration. Generally, dispersions are prepared by incorporating the active compound into a sterile vehicle which contains a basic dispersion medium and the other desired ingredients. In the case of sterile powders for the preparation of sterile injectable solutions, the preparation is dried, e.g., by vacuum drying and/or freeze-drying.

Pharmaceutical compositions adapted for topical administration may include, but are not limited to, compositions in the form of skin care, skin cleansing, or anti-wrinkle products, shampoos, make-up, conditioners, lotions, aerosols, gels, mousses, dyes, or bleaches. These compositions may contain one or more conventional cosmetic or dermatological additives or adjuvants, including, but not limited to, fillers, surfactants, thixotropic agents, antioxidants, preserving agents, dyes, pigments, fragrances, thickeners, vitamins, hormones, moisturizers, UV absorbing organic sunscreens, UV scattering inorganic sunscreens, wetting agents, cationic, anionic, nonionic or amphoteric polymers, and hair coloring active substances. These adjuvants are well known in the field of cosmetics and are described in many publications, for example see Harry's Book of Cosmeticology, $8^{th}$ edition, Martin Rieger, ed., Chemical Publishing, New York (2000). Exemplary compositions are described in, for example, in U.S. Pat. Application 2005008604, U.S. Pat. Application 20050025725 and U.S. Pat. Application 20040120918 which are herein incorporated by reference.

In certain embodiments, the pharmaceutical compositions of this invention can include one or more chemical penetration enhancers (as described, for example, in International Publication No. WO2005009510).

Exemplary chemical penetration enhancers include, but are not limited to, 1-dodecyl pyrrolidone, benzyl dimethyl dodecyl ammonium chloride, cocamidopropyl betaine, cocamidopropyl hydroxysultaine, oleyl betaine, cineole, cetyl trimethyl ammonium bromide, dodecyl amine, dodecyl pyridinium chloride, hexadecyl trimethyl ammoniopropane sulfonate, isopropyl myristate, lauric acid, limonene, linoleic acid, linolenic acid, menthol (terpene), methyl laurate, 1-methyl-2-pyrrolidone, N-lauryl sarcosine (CAS number 137-16-6, also called sodium lauroyl sarcosinate), nicotine sulfate, oleic acid, octyl trimethyl ammonium bromide, polyethyleneglycol dodecyl ether, 1-phenyl piperazine, sorbitan monolaurate, sodium lauryl ether sulfate, sodium dodecyl sulfate, sodium oleate, sodium octyl sulfate, tetracaine, and Tween-20™.

Chemical penetration enhancers increase skin permeability and are known in the art (see, for example, Shah et al. "Skin Penetration Enhancement: Clinical pharmacological and regulatory considerations." Pharmaceutical Skin Penetration Enhancement, ed. K. Walters. 1993, New York, Basel, Hong Kong: Marcel Dekker. 417-427).

The present peptides may be used in cosmetic compositions either as the peptides themselves or in the form of a premix in a suitable excipient and they may be used in the form of a solution, dispersion, emulsion, paste or powder. They may individually or with other active substances, including but not limited to those specifically described herein, be carried by cosmetic vectors such as macro-, micro- or nanocapsules, liposomes or chylomicrons, macro-, micro- or nanoparticles or microsponges. They may also be adsorbed on powdered organic polymers, talcs, bentonites and other inorganic carriers.

The peptides may be used in any form or in a form that is bound, incorporated, absorbed in or adsorbed on macro-, micro- and nanoparticles, macro-, micro- and nanocapsules for the treatment of textiles, synthetic or natural fibers, wools and all materials liable to be used in the manufacture of clothing or underwear for the day or night, intended for contact with the skin, such as pantyhose, underwear, handkerchiefs and wipes, in order to exert a cosmetic effect through the contact between the textile and skin and enable continuous topical delivery.

The peptides can be used in topical compositions (e.g., therapeutic or cosmetic compositions) at concentrations ranging from 0.00001% (w/w) ("w/w" is weight/weight) and 10% (w/w) (e.g., between about 0.0001% (w/w) and 1% (w/w)). Another useful range is from about 0.001% and about 5% (w/w). The peptides may also be used in the range of about 1 ppm to about 500 ppm (e.g., about 100 to about 400 ppm).

Compositions for oral administration typically include an inert or edible diluent or edible carrier. Such compositions can be formulated in various ways, e.g., in liquid, capsule, or tablet form. Pharmaceutically compatible binding agents, and/or adjuvant materials can be included as part of the composition. The tablets, pills, capsules, troches and the like can contain any one or more of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For inhalation administration (e.g., for application to wounded tissues, such as mucosa, within the nasal passages, nasopharynx, trachea or lungs or), the present compositions are delivered in the form of a wet or dry aerosol spray, e.g., from a pressured container or dispenser which contains a suitable propellant, e.g., a gas such as carbon dioxide, or a nebulizer.

Systemic administration can also be by transmucosal or transdermal routes. For transmucosal or transdermal administration, penetrants appropriate to the barrier to be permeated are typically used in the formulation. A number of such penetrants are generally known in the art, and include, for example, for transmucosal administration, detergents, bile salts, and fusidic acid derivatives. Administration may also be facilitated by iontophoresis, microneedles and other devices designed to enhance transdermal penetration.

Transmucosal administration can be accomplished through the use of nasal sprays or suppositories (e.g., using conventional suppository bases such as cocoa butter and other glycerides). For transdermal administration, the active compounds are formulated into ointments, salves, gels, or creams as generally known in the art.

Such compositions can also be formulated with carriers that will protect the compositions against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polycarbonates, and polylactic acid. The materials can also be obtained commercially, e.g., from Alza Corporation and Nova Pharmaceuticals, Inc. Liposomal suspensions (including liposomes targeted to particular cells (e.g., targeted to infected cells) with monoclonal antibodies) can also be used to prepare pharmaceutical compositions. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals. In one embodiment of the fibronectin fragments and peptide derivatives of fibronectin fragments of the invention, the dosage unit form is about 0.1 to 5 mg of lyophilized peptide or peptide derivative. In another embodiment of the fibronectin fragments and peptide derivatives of fibronectin fragments of the invention, the dosage unit form is about 1 mg of lyophilized peptide or peptide derivative.

Toxicity and therapeutic efficacy of active compounds and pharmaceutical compositions can be determined by standard pharmaceutical procedures in cell cultures or experimental animals. For example, such procedures are routinely applied for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are generally preferred. The data obtained from the cell culture assays and animal studies (including those described in the examples, below) can be used in formulating a range of dosage for use in humans or other intended subjects. The dosage of such compounds is usually selected to produce a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. Thus, for example, a dose may be initially established in animal models to achieve a circulating plasma concentration range that includes the EC50 (i.e., the concentration of the test compound which achieves a half-maximal response) as determined in cell culture. Such information can be used to more accurately determine useful doses in humans. Levels in plasma may be measured, for example, by high performance liquid chromatography, or by other suitable analysis method adapted for the compound of interest.

As noted, peptides (e.g., synthetic or recombinantly produced peptides) with growth factor-binding and/or -enhancing/inhibiting activity can be incorporated into a tissue engineered product. FN domains that promote fibroblast migration can also be included. Preferably, the products are robust (i.e., relatively resistant to rapid degradation). They can be used, for example, in treating wounds, including acute or non-healing wounds (e.g., chronic ulcers). Patients amenable to treatment are described further below. Alternatively or in addition, growth factor-binding and/or enhancing peptides can be tethered to a biocompatible polymer for delivery of one or more growth factors to a cell, tissue or organ in need of treatment or for endogenous localization of growth factors. Alternatively or in addition, growth factor-binding and/or enhancing peptides can be incorporated in a polymer or nonpolymer biomaterial for controlled release to an acute or non-healing wound.

We have developed an engineered ECM that is conductive and inductive of new tissue formation in porcine cutaneous wounds utilizing molecular domains C, H, and HV or cell adhesion peptides of the blood protein fibronectin (FN) tethered to an intramolecularly crosslinked hyaluronan (HA) hydrogel. Thus, in one implementation, the invention includes an engineered ECM that includes a fragment of a fibronectin (e.g., a plasma fibronectin) or a biologically active variant thereof. The fragment can be tethered to (e.g., covalently or non-covalently bound to) a hydrogel (e.g., an HA hydrogel) and can be a fragment that binds and/or enhances a polypeptide growth factor. The fragment can be tethered according to attachment methods discussed in U.S. Pat. Application 20050282747, the contents of which are incorporated herein in their entirety.

The naturally-occurring ECM is comprised of diverse constituents such as glycoproteins, proteoglycans, complex carbohydrates, and other molecules. Major functions of the ECM include, but are not limited to, providing structural support, tensile strength or cushioning; providing substrates and pathways for cell adhesion and cell migration; and regulating cellular differentiation and metabolic function. ECM proteins include, for example, collagens, elastin, fibronectin, laminin, proteoglycans, vitronectin, thrombospondin, tenascin (cytoactin), entactin (nidogen), osteonectin (SPARC), anchorin CII, chondronectin, link protein, osteocalcin, bone sialoprotein, osteopontin, epinectin, hyaluronectin, amyloid P component, fibrillin, merosin, s-laminin, undulin, epilligrin, and kalinin.

The featured tissue engineered product (e.g., the engineered ECM) can include biological and/or synthetic components. It can include a biopolymer (e.g., hyaluronan (HA), a glycosaminoglycan (GAG), fibrinogen, laminin, or collagen). The biocompatible polymer can be a synthetic biodegradable polymer, many of which are known in the art. For example, the biodegradable polymer can be a poly(lactide), a poly(glycolide), a poly(lactide-coglycolide), a poly(lactic acid), a poly(glycolic acid), a poly(lactic acid-co-glycolic acid), a poly(caprolactone), a polycarbonate, a polyesteramide, a polyanhydride, a poly(amino acid), a poly(ortho ester), a polycyanoacrylate, a polyamide, a polyacetal, a poly(ether ester), a copolymer of poly(ethylene glycol) and a poly(ortho ester), a poly(dioxanone), a poly(alkylene alkylate)s, a biodegradable polyurethane, or any blend or copolymer thereof. Other useful polymers include an alginate polymer and a carboxy-vinyl polymer (e.g., a polymer including at least 90% acrylic acid monomers and about 0.1% to about 5.0% of a difunctional crosslinking agent).

A tissue engineered "smart" matrix that would be conductive and inductive of tissue cell repopulation of a wound site and the development of new tissue, respectively, can be composed of GFs, or active fragments thereof, in the context of an appropriate ECM that are required for optimal wound repair. In addition, FN GF-binding domain(s) may provide a useful tool for engineering many other GF localization (from endogenous or exogenous sources) and/or delivery systems for soft or hard tissue repair, augmentation and regeneration. Furthermore, growth factor FN/VN-binding peptides or molecularly engineered derivatives of the FN and VN GF-binding domains might become strongly inhibitory of GF activity and thus useful for proliferative or fibrotic disorders such as cancer, pulmonary fibrosis, GI or GU stenosis, burn contractures and autoimmune generated sclerosis.

EngECM can be generated with or without growth factors, or active fragments thereof (e.g., growth factors and fragments described herein). In the former case, the dosage of growth factors in the engECM can vary, e.g., as described below, 100 ng/ml (15 ng total per wound) of PDGF-BB added to 2:1 engineered ECM enhanced granulation formation at 4 days after injury and application of material. In the latter case, when placed in the vicinity of an endogenous supply of growth factors, the growth factors can be recruited by the matrix.

The invention further encompasses nucleic acid molecules, including DNA and RNA molecules, that encode the polypeptides described herein. The nucleic acid molecules can be formulated in physiologically acceptable compositions for administration. The invention also features vectors that include the present nucleic acid constructs. Of particular benefit are expression vectors, especially those for expression in eukaryotic cells. Such vectors can, for example, be viral, plasmid, cosmid, or artificial chromosome (e.g., yeast artificial chromosome) vectors. Typically, plasmids are circular, dsDNA elements that include one or more cloning sites for insertion of selected DNA sequences, e.g., coding sequences. Such plasmids may include a functional origin of replication and thus are replication competent, or may be replication defective.

In addition to plasmids, viral vectors (e.g., replication defective retroviruses, lentiviruses, adenoviruses and adeno-associated viruses) can also be advantageously used. A large number of such viral vectors have been developed having a broad variety of different properties. For example, such viral vectors may be replication defective retroviruses, adenoviruses and adeno-associated viruses. Techniques and procedures for producing recombinant retroviruses and for infecting cells in vitro or in vivo with such viruses are provided in Current Protocols in Molecular Biology, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are well known to those skilled in the art. Examples of suitable packaging virus lines include psi.Crip, psi.Cre, psi.2 and psi.Am. The genome of adenovirus can be manipulated such that it encodes and expresses a nucleic acid construct, as described herein, but is inactivated in terms of its ability to replicate in a normal lytic viral life cycle. (see, e.g., Berkner et al., BioTechniques 6:616, 1988; Rosenfeld et al., Science 252:431-434, 1991; and Rosenfeld et al., Cell 68:143-155, 1992). Suitable adenoviral vectors derived from the adenovirus strain Ad type 5 d1324 or other strains of adenovirus (e.g., Ad2, Ad3, Ad7 etc.) are well known to those skilled in the art. Alternatively, an adeno-associated virus vector such as that described in Tratschin et al. (Mol. Cell. Biol. 5:3251-3260, 1985) can be used to express a transactivator fusion protein. Other viral vector alternatives include lentiviral vectors. Such vectors and their preparation and use are described, for example, in U.S. Pat. Nos. 6,924,123; 6,863,884; 6,830,892; 6,818,209; 6,808,923; 6,799,657, all of which are incorporated herein in their entireties.

The vectors of the invention can advantageously include a polypeptide fragment described herein. Other elements included in the design of a particular expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

The vectors described herein can be introduced into cells or tissues by any one of a variety of known methods within the art. Such methods are described for example in Sambrook et al., Molecular Cloning: A Laboratory Manual, Cold Spring Harbor Laboratory, New York (1992), which is hereby incorporated by reference. See, also, Ausubel et al., Current Protocols in Molecular Biology, John Wiley and Sons, Baltimore, Md. (1989); Hitt et al., "Construction and Propagation of Human Adenovirus Vectors," in Cell Biology: A Laboratory Handbook, Ed. J. E. Celis., Academic Press. 2nd Edition, Volume 1, pp: 500-512, 1998; and Hitt et al., "Techniques for Human Adenovirus Vector Construction and Characterization," in Methods in Molecular Genetics, Ed. K. W. Adolph, Academic Press, Orlando, Fla., Volume 7B, pp: 12-30, 1995. The methods include, for example, stable or transient transfection, lipofection, electroporation and infection with recombinant viral vectors. The term "transfecting" or "transfection" is intended to encompass all conventional techniques for introducing nucleic acid into host cells, including calcium phosphate co-precipitation, DEAF-dextran-mediated transfection, lipofection, electroporation and microinjection. Suitable methods for transfecting host cells can be found in Sambrook et al. (Molecular Cloning: A Laboratory Manual, 2nd Edition, Cold Spring Harbor Laboratory press (1989)), and other laboratory textbooks.

For plant cells, a Ti plasmid or viral vector is often used. For example, such plasmids and viral vectors can be used to transfect host plant cells via *Agrobacterium tumefaciens*-mediated transfection (for plant cells susceptible to *A. tumefaciens* infection), or can be directly inserted in cells, e.g., using microinjection, particle bombardment, or electroporation. In other methods, protoplasts can be made from plant cells and then transfected.

The number of host cells transformed with a nucleic acid constructs of the invention will depend, at least in part, upon the type of recombinant expression vector and the type of transfection technique used. Nucleic acid can be introduced into a host cell transiently, or for long-term expression. For long-term expression, the nucleic acid is stably integrated into the genome of the host cell or remains as a stable episomal element.

For integration of nucleic acid into host cell DNA, typically a gene is used that encodes a selectable marker (e.g., drug resistance) is introduced into the host cells along with the nucleic acid of interest. A variety of such selectable markers are commonly used, such as the drugs hygromycin and neomycin. Selectable markers can be introduced on a separate plasmid or other vector from the nucleic acid of interest or, are introduced on the same vector. Host cells transfected with a nucleic acid construct of the invention (e.g., a recombinant expression vector) and a gene for a selectable marker can be identified by selecting for cells using the selectable marker.

The present nucleic acid constructs can be introduced into eukaryotic cells growing in culture in vitro by conventional transfection techniques (e.g., calcium phosphate precipitation, DEAE-dextran transfection, electroporation, and other methods). Cells can also be transfected in vivo, for example by application of a delivery mechanism suitable for introduction of nucleic acid into cells in vivo, such as viral vectors (see e.g., Ferry et al., Proc. Natl. Acad. Sci. USA 88:8377-8381, 1991, and Kay et al., Human Gene Therapy 3:641-647, 1992), adenoviral vectors (see e.g., Rosenfeld, Cell 68:143-155, 1992; and Herz and Gerard, Proc. Natl. Acad. Sci. USA 90:2812-2816, 1993), receptor-mediated DNA uptake (see e.g., Wu and Wu, J. Biol. Chem. 263: 14621, 1988; Wilson et al., J. Biol. Chem. 267:963-967, 1992; and U.S. Pat. No. 5,166,320), direct injection of DNA (see e.g., Acsadi et al., Nature 332:815-818, 1991; and Wolff et al., Science 247:1465-1468, 1990) or particle bombardment (see e.g., Cheng et al., Proc. Natl. Acad. Sci. USA 90:4455-4459, 1993; and Zelenin et al., FEBS Letters 315: 29-32, 1993). Thus, in the present invention, cells can be transfected in vitro or ex vivo, and the expressed peptide can be isolated there from by methods known in the art. The cells can also be administered to a subject or, alternatively, cells can be directly modified in vivo. In any of these situations, the nucleic acid construct used to express the peptide can include a signal sequence to facilitate export from the cell.

Another aspect of the invention pertains to host cells into which a nucleic acid construct of the invention has been introduced, i.e., a "recombinant host cell." It is understood that the term "recombinant host cell" refers not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell, although eukaryotic cells are preferred. Exemplary eukaryotic cells include mammalian cells (such as Chinese hamster ovary cells (CHO) or COS cells). Other suitable host cells are known in the art.

It is not intended that the present invention be limited by the particular nature of the therapeutic preparation, so long as the preparation comprises an appropriate fragment of fibronectin that binds a polypeptide growth factor or that has intrinsic survival or growth factor activity or an appropriate fragment of a growth factor that binds fibronectin. For example, such compositions can be provided together with physiologically tolerable liquid, gel or solid carriers, diluents, adjuvants and/or excipients.

These therapeutic preparations can be administered to mammals for veterinary use, such as with domestic animals, and clinical use in humans in a manner similar to other therapeutic agents. In general, the dosage required for therapeutic efficacy will vary according to the type of use and mode of administration, as well as the particularized requirements of individual hosts.

Such compositions are typically prepared as liquid solutions or suspensions, or in solid forms. Formulations can include such normally employed additives such as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained release formulations, or powders, and typically contain 1%-95% of active ingredient, preferably 2%-70%.

The compositions are also prepared as injectables, either as liquid solutions or suspensions; solid forms suitable for solution in, or suspension in, liquid prior to injection may also be prepared.

The fragments of the present invention are often mixed with diluents or excipients which are physiologically tolerable and compatible. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH buffering agents.

Additional formulations which are suitable for other modes of administration, such as topical administration, include salves, tinctures, creams, lotions, and, in some cases, suppositories. For salves and creams, traditional binders, carriers and excipients may include, for example, polyalkylene glycols or triglycerides.

Methods of Use

The fibronectin fragments and peptide derivatives of fibronectin fragments described herein are useful in promoting tissue regeneration, e.g., wound healing, and in cosmetic and therapeutic formulations for the prevention and treatment of poor skin appearance related to, for example, aging. Use in cell culture is also described. The polypeptides (or nucleic acids or expression vectors encoding them or cells expressing them) can be incorporated into, for example, therapeutic formulations for the indications described herein as well as into products and compositions for improving, for example, skin appearance and/or feel of skin exhibiting signs of skin aging.

For example, compositions of the present invention are useful for regulating the appearance of skin due to wrinkles and UVB photodamage by providing visual improvement in skin appearance following application of the composition to the skin. Generally speaking, compositions of the present invention which further contain particulate materials will be most useful for providing the immediate visual improvement.

The invention features cosmetic treatments including those for prophylactically regulating a skin condition and those for therapeutically regulating a skin condition. "Signs of skin aging," "poor skin appearance," and other phrases similarly referring to, for example, symptoms of aging and the like include, but are not limited to, all outward visibly and tactilely perceptible manifestations as well as any other macro or micro effects due to skin aging. Such signs may be induced or caused by intrinsic factors and/or extrinsic factors, e.g., chronological aging and/or environmental damage (e.g., UVB photodamage, exposure to pollutants, and poor diet). These signs may result from processes which include, but are not limited to, the development of textural discontinuities such as wrinkles and coarse deep wrinkles, skin lines, crevices, bumps, large pores (e.g., associated with adnexal structures such as sweat gland ducts, sebaceous glands, or hair follicles), or unevenness or roughness, loss of skin elasticity (loss and/or inactivation of functional skin elastin), sagging (including puffiness in the eye area and jowls), loss of skin firmness, loss of skin tightness, loss of skin recoil from deformation, discoloration (including undereye circles), blotching, sallowness, hyperpigmented skin regions such as age spots and freckles, keratoses, abnormal differentiation, hyperkeratinization, elastosis, collagen breakdown, and other histological changes in the stratum corneum, dermis, epidermis, the skin vascular system (e.g., telangiectasia or spider vessels), and underlying tissues, especially those proximate to the skin. Particularly preferred in accordance with the present invention, the signs of skin aging are wrinkles and the compositions of the present invention are, in certain preferred embodiments, useful in fighting, treating or preventing wrinkles.

Wrinkles can result from numerous causes. For example, wrinkles can be caused from the natural aging process of the skin, from smoking, and from exposure to ultraviolet radiation (e.g., from chronic sun exposure). Wrinkles can be classified as described in Kligman et al. (Br. J. Derm. 113:37-42, 1985), herein incorporated by reference. Kligman classifies wrinkles into three classes: linear wrinkles, glyphic wrinkles, and crinkles, and any of these types of wrinkles, regardless of their cause, can be treated as described herein. Aside from wrinkles per se, the present compositions can be used to improve the skin's appearance.

The methods disclosed herein are useful to prevent or treat or reduce wrinkles, including UV-induced wrinkles, and/or to improve skin quality and appearance in a subject. The methods can be carried out by administering to the subject a composition containing a fibronectin fragment or a biologically active variant thereof. An exemplary treatment method can include locating a wrinkle or a potential site of wrinkling and applying a composition described herein.

As used herein, prophylactically regulating a skin condition includes delaying, minimizing and/or preventing visible and/or tactile discontinuities in skin (e.g., texture irregularities in the skin which may be detected visually or by feel), including signs of skin aging.

As used herein, therapeutically regulating skin condition includes ameliorating, e.g., diminishing, minimizing and/or effacing, discontinuities in skin, including signs of skin aging. Some of the products produced using the compositions of the present invention and indeed the compositions themselves may be used for prophylactically or therapeutically regulating a skin condition.

In certain preferred aspects, the present invention is useful for improving the physiological state and/or the physical appearance of human skin, in particular to reduce the signs of skin aging that are generated by sun exposure (e.g., UVB photodamage), physical and hormonal stress, abrasion, nutritional effects and other similar causes. The compositions may often be used to prevent the signs of aging and/or to treat them in order to afford the consumer who uses them, a more youthful appearance.

All terms such as "skin aging," "signs of skin aging," "poor skin appearance," "topical application," and the like are used in the sense in which they are generally and widely used in the art of developing, testing and marketing cosmetic and personal care products. "Wrinkles" means furrows in the otherwise smooth surface of the facial skin, visible to the naked eye, in the average depth of 50 to more than 200 µm and essentially appearing with progressive age. The term "cosmetic composition" in accordance with the present invention relates to a formulation that can be used for cosmetic purposes, purposes of hygiene or as a basis for delivery of one or more pharmaceutical ingredients. This includes cosmetics, personal care products and pharmaceutical preparations. It is also possible that these formulations are used for two or more of these same purposes at one time. A medicated dandruff shampoo, for example, has pharmacological properties and is used as a personal care product to provide clean hair. These compositions may also include additional ingredients such as a dermatologically acceptable carrier. "Cosmetics," as used herein, include without limitation, lipstick, mascara, rouge, foundation, blush, eyeliner, lipliner, lip gloss, facial or body powder, sunscreens and blocks, nail polish, mousse, sprays, styling gels, nail conditioner, whether in the form of creams, lotions, gels, ointments, emulsions, colloids, solutions, suspensions, compacts, solids, pencils, spray-on formulations, brush-on formulations and the like. "Personal care products" include, without limitation, bath and shower gels, shampoos, conditioners, cream rinses, hair dyes and coloring products, leave-on conditioners, sunscreens and sunblocks, lip balms, skin conditioners, cold creams, moisturizers, hair sprays, soaps, body scrubs, exfoliants, astringents, depilatories and permanent waving solutions, antidandruff formulations, antisweat and antiperspirant compositions, shaving, pre-shaving and after shaving products, moisturizers, deodorants, cold creams, cleansers, skin gels, rinses, whether in solid, powder, liquid, cream, gel, ointment, lotion, emulsions, colloids, solutions, suspensions, or other form. "Pharmaceutical preparations" in accordance with the present invention include, without limitation, carriers for dermatological purposes, including topical and transdermal application of pharmaceutically active ingredients. These can be in the form of gels, patches, creams, nose sprays, ointments, lotions, emulsions, colloids, solutions, suspensions, powders and the like. Compositions in accordance with the invention include cosmetics, personal care products and pharmaceutical preparations.

The invention features methods for promoting tissue regeneration, including, for example, wound healing. As used herein, tissue regeneration is used to refer to the replacement of damaged tissue by the proliferation and differentiation of cells into a tissue. Tissue damage can occur by any means, including physical injury, disease, and infection. As described herein, "wound-healing" is used as a non-limiting example of tissue regeneration.

The primary goal in the treatment of wounds is to achieve wound closure. Open cutaneous wounds represent one major category of wounds and include thermal and/or chemical burn wounds, neuropathic ulcers, pressure sores, venous stasis ulcers, and diabetic ulcers. Open cutaneous wounds routinely heal by a process which comprises six major components: i) inflammation, ii) fibroblast proliferation, iii) blood vessel proliferation, iv) connective tissue synthesis v) epithelialization, and vi) wound contraction. Wound healing is impaired when these components, either individually or as a whole, do not function properly. Numerous factors can affect wound healing, including malnutrition, infection, pharmacological agents (e.g., actinomycin and steroids), diabetes, and advanced age (see Hunt and Goodson in Current Surgical Diagnosis & Treatment (Way; Appleton & Lange), pp. 86-98, 1988).

The term "wound" refers broadly to injuries to the skin and subcutaneous tissue initiated in different ways (e.g., pressure sores from extended bed rest and wounds induced by trauma) and with varying characteristics as well as to injuries of other tissues and bone, including tissues and bone in or around the vicinity of a primary wound site. Of course, wounds can also be made surgically or by disease (e.g. cancer). Wounds may be classified into one of four grades depending on the depth of the wound: i) Grade I: wounds limited to the epithelium; ii) Grade II: wounds extending into the dermis; iii) Grade III: wounds extending into the subcutaneous tissue; and iv) Grade IV (or full-thickness wounds): wounds wherein bones are exposed (e.g., a bony pressure point such as the greater trochanter or the sacrum). The term "partial thickness wound" refers to wounds that encompass Grades I-III; examples of partial thickness wounds include thermal or chemical burn wounds, pressure sores, venous stasis ulcers, and diabetic ulcers. The term "deep wound" is meant to include both Grade III and Grade IV wounds. The present invention contemplates treating all wound types, including deep wounds and chronic wounds.

The phrases "promote wound healing," "enhance/improve wound healing," and the like refer to either the induction of the formation of granulation tissue and/or the induction of epithelialization (i.e., the generation of new cells in the epithelium), and/or reduction of scarring. Wound healing is conveniently measured by decreasing wound area. It is not intended that phrases such as "promote wound healing" or "enhance/improve wound healing" require a quantitative comparison with controls. In the case of treatment of a chronic wound, it is sufficient that evidence of wound healing begins after treatment. Many traumatic wounds and cancer extirpations must be left open to heal by secondary intention, and patients having such wounds and extirpations can be treated with the compositions described herein that promote wound healing.

The phrase "therapeutically effective amount" of the fibronectin fragments or peptide derivatives of fibronectin fragments of the invention, when referring to wound healing, promoting wound healing or enhancing wound healing, is that amount that promotes induction of the formation of granulation tissue and/or the induction of epithelialization and/or reduction of scarring. For example, fibronectin fragments or peptide derivatives of fibronectin fragments of the invention can be used to promote would healing in i.v. formulations in an amount of from about 0.1 µg/kg to about 1 mg/kg of patient body weight; in some embodiments, from about 1 µg/kg to about 1 mg/kg of patient body weight; in some embodiments, from about 1 µg/kg to about 0.1 mg/kg of patient body weight; in some embodiments, from about 0.01 mg/kg to about 1 mg/kg of patient body weight; and in some embodiments, from about 0.01 mg/kg to about 0.1 mg/kg of patient body weight.

The incidence of chronic wounds, sometimes referred to as non-healing wounds, is rising due to events such as aging populations; an increase in age-related diseases in those populations; an increase in the incidence of AIDS; an increase in the incidence of diabetes, and an increase in radiation wounds secondary to cancer intervention. Patients who have chronic wounds, including those associated with the events just described, can be treated with the compositions described herein that promote wound healing.

The present compositions can be used either instead of or to supplement existing wound-care procedures such as skin grafting and tissue flaps, debridement, and the administration of anti-inflammatory, antibacterial and/or anti-pain medications. Patients amenable to treatment include those who have chronic dermal ulcerations, as can occur in association with diabetes. Diabetic ulcers, however, are just one part of the chronic wound picture. It is estimated that 5.5 million people in the United States have chronic, nonhealing wounds.

The methods of the invention include a step of administering to a patient a therapeutically effective amount of a pharmaceutical composition comprising a peptide fragment of fibronectin, or a biologically active variant thereof, as described herein. The peptide fragment of fibronectin, or the biologically active variant thereof, can be present in a complex with one or more growth factors. The methods can optionally include a step of identifying a patient in need of treatment. Such patients include patients who are suffering from a surgical extirpation or incision of the skin, mucosa, underlying connective tissue, fascia, nerve or muscle; patients who are suffering from a traumatic laceration or tissue loss of the skin, mucosa, underlying connective tissue, fascia, nerve, muscle or bone; and patients who are suffering from a thermal or chemical burn or ulceration of the skin, mucosa, underlying connective tissue, fascia, nerve or muscle.

Suitable formulations are described herein and, generally, take the form of a solution, ointment or salve. The fragments of fibronectin, whether or not complexed with a growth factor, can also be administered by way of their inclusion in a biomaterial, such as a synthetic polymer, an engineered ECM, a bandage, dressing, compress, or the like.

By other methods of the invention, one can localize an endogenous growth factor to a tissue of a patient. These methods can be carried out by administering, to the patient, a therapeutically effective amount of a composition that includes a fragment of fibronectin or a biologically active variant thereof, as described herein. As in the more specific treatment methods described herein, these compositions can be administered by way of topical application of a pharmaceutical composition, a biomaterial, or a solid support, or by other local and systemic routes (e.g., orally, intravenously, intramuscularly, subcutaneously, intradermally, pericutaneously, or transmucosally). These methods can be described as methods of delivering one or more growth factors to a patient. The methods can optionally include a step of identifying a patient in need of treatment. Such patients include patients who are suffering from an injury to a tissue, a loss of a tissue or a disorder resulting in tissue disfigurement or dysfunction. More specifically, the patient can be suffering from an injury or loss to the brain, spinal cord or nerves or a disorder resulting in brain, spinal cord or nerve dysfunction; an injury or loss to the heart or blood vessels or a disorder resulting in heart or blood vessel dysfunction; an injury or loss to the lung, nasopharyngeal tract, sinuses, trachea or airways or a disorder resulting in lung, nasopharyngeal tract, sinus, trachea or airway dysfunction; an injury or loss to the gastrointestinal tract, liver or pancreas or a disorder resulting in gastrointestinal tract, liver or pancreas dysfunction; an injury or loss to a kidney, ureters, bladder or urethra or a disorder resulting in kidney, ureters, bladder or urethra dysfunction; an injury or loss to cartilage, synovium, meniscus, ligament, tendon or nucleus pulposis or a disorder resulting in cartilage, synovium, meniscus, ligament, tendon or nucleus pulposis dysfunction; an injury or loss to bone; an injury or loss to lips, tongue or gums or a disorder resulting in lip, tongue and gum dysfunction; an injury or loss to the subcutaneous tissue or a disorder resulting in subcutaneous tissue dysfunction.

In Vitro and In Vivo Model Systems

Test compounds may be further characterized in in vitro and in vivo model systems. For example, test compounds can be tested for effects on cell migration using Adult Human Dermal Fibroblasts (ADHF), human microvascular endothelial cells (HEDMC), or other cell types. For example, test compounds can be tested for effects on wound healing using the porcine re-injury model, excisional wound model in pigs or mice, hot comb burn wound model in pigs or rats, vertical injury progression burn models in pigs, chemical burns in pigs.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Studies of Topical Treatment of Porcine Burns with PDGF-BB and Formula I Peptide Formulations Four female, 20-30 kg, domestic pigs were used for cutaneous wound procedures.

Study Protocol: The animals were sedated with Talazine (Tiletamine and Zolazepam, Fort Dodge Lab, Fort Dodge, Iowa) 5 mg/kg IM. The pigs were then intubated endotracheally and maintained under a surgical plane of anesthesia with isoflurane 0.5-2.5% in room air. The flank and back hair were clipped with electric hair clippers and the skin was scrubbed with a povidone iodine solution.

Standardized deep partial-thickness burns were created on the animals' backs and flanks by applying a 2.5-cm by 2.5-cm, 150-gram aluminum bar preheated in hot water to 80° C. The burns were created on either side of the vertebral column between the forelegs and hind legs. The heated bar was wiped dry just prior to application to prevent water droplets from creating a steam burn on the skin. The bar was then placed at a vertical position perpendicular to the skin's surface and applied for a period of 20 seconds with all pressure supplied by gravity. This burn model results in damage to the upper 30-50% of the dermis and has been shown to be highly reproducible (Singer et al., Acad. Emerg. Med. 7:1-6, 2000). 24 burns were evenly distributed on both sides of the back of four pigs. Since pigs do not form blisters after thermal injury, debridement of the necrotic epidermis was performed immediately after injury in order to simulate burns in humans where blisters may form and subsequently rupture (Singer et al., Acad. Emerg. Med., 7:114-119, 2000). Debridement was performed by gently rubbing dry gauze against the surface of the burn until the necrotic epidermis was peeled away from the entire burn surface. Interventions: On the back skin of each pig, equal sets of 4 burns were randomly treated with one of the 6 study treatments. Each treatment of pluronic lecithin organogel ("PLO") gels, PLO gels containing PDGF-BB, PLO gels containing cP12 or cNP8 and PLO gels containing either cP12 or cNP8 and PDGF-BB, was applied to 4 burn wounds per pig after either 24 hour post-burn or 48 hour post-burn. Peptides selected for testing were synthesized in a GMP faculty (American Peptide, Vista, Calif.) and diluted in sterile, endotoxin-free PBS with sterile, endotoxin-free 2% porcine serum (HyClone, Logan, Utah) to avoid peptide loss via nonspecific surface adsorption. Sterile, endotoxin-free recombinant PDGF-BB (R&D Systems) was also diluted in PBS with 2% porcine serum. Final concentrations of peptides with and without PDGF-BB were compounded in a 30% pluronic lecithin gel using a sterile, endotoxin-free PLO kit (Transderma, Coquitlam, BC, Canada). PBS with 2% porcine serum in a 30% pluronic gel was used as a treatment control. Wounds received 150 μl of treatment gels applied topically on a daily basis for the first week and twice weekly thereafter. Then burns were covered with dry non-adherent gauze (Telfa, Kendall Company, Mansfield, Mass.) and the burned areas covered with a gauze bandage roll (Conform, Kendall Healthcare Products Company, Mansfield, Mass.) and an adhesive elastic bandage (Elastoplast, Beiersdorf-Jobst, Inc., Rutherford College, N.C.). In order to prevent dressing removal, staples were applied to the periphery of the dressings. Dressing changes were applied as above after each treatment application. All of the animals were treated with a Fentanyl transdermal patch post operatively for analgesia management.

Survival surgery of pigs and wound site harvest was done under general anesthesia. Pigs were fasted for 24 hours before the surgical procedures. Atropine was given pre-op at a dose of 0.05 mg/kg. For induction of general anesthesia 4.4 mg/kg Telazol and, 2.2 mg/kg Xylazine and 0.22 mg/kg Butorphanol were administered IM. The animal was then intubated and held at the stage of surgical anesthesia with Isoflurane (1-3%) and oxygen. Since covered cutaneous wounds cause minor pain to humans that require at most acetaminophen, animals were treated likewise receiving 10-20 mg/kg acetaminophen twice daily after survival surgery.

Euthanasia is accomplished with intravenous 100 mg/kg pentobarbital and 2 mg/kg xylazine.

Figure 6:
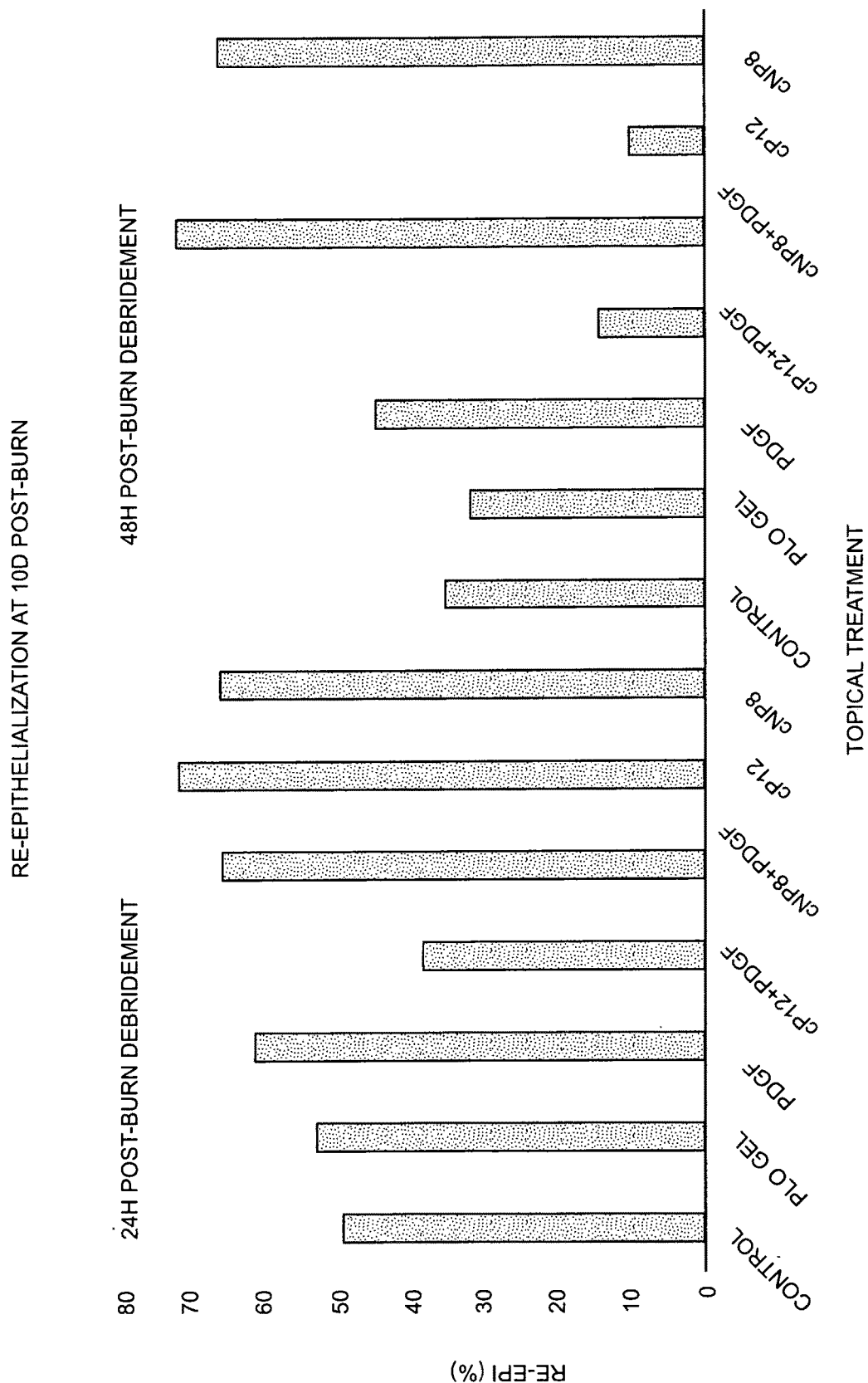
FIG. 6 shows a comparison of effectiveness of cP12 and cNP8 peptide for promoting re-epithelialization of burn wounds with topical treatment in a porcine model.

As shown in FIG. 6, re-epithelialization of 48-hour debrided wounds, 10 days after wounding was markedly increased for cNP8-treated wounds, as compared to control or cP12-treated wounds.

Figure 7:
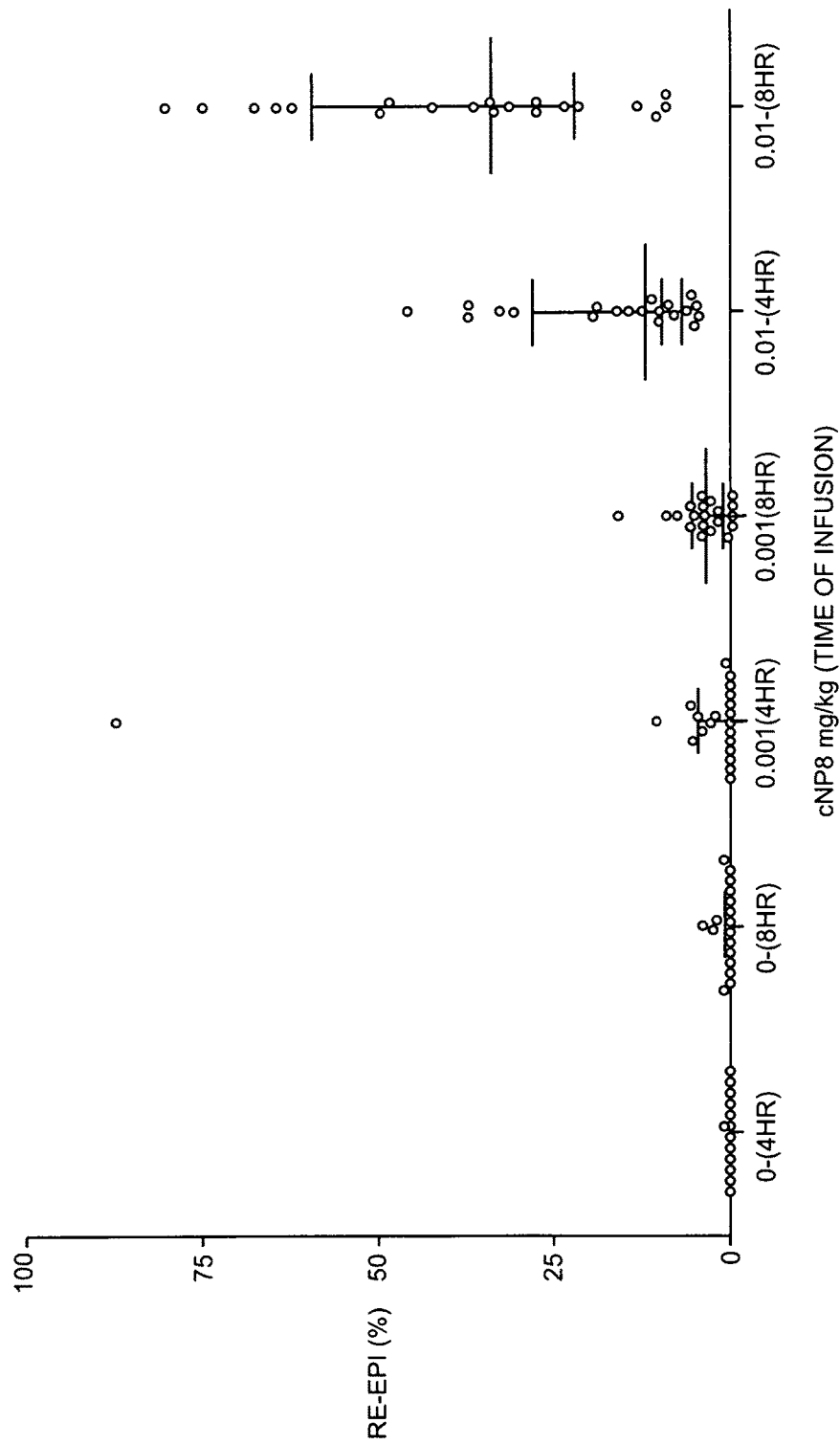
FIG. 7 shows the increase of re-epithelialization on day 10 at the wound site with intravenous cNP8 treatment in a porcine burn model.
Figure 8:
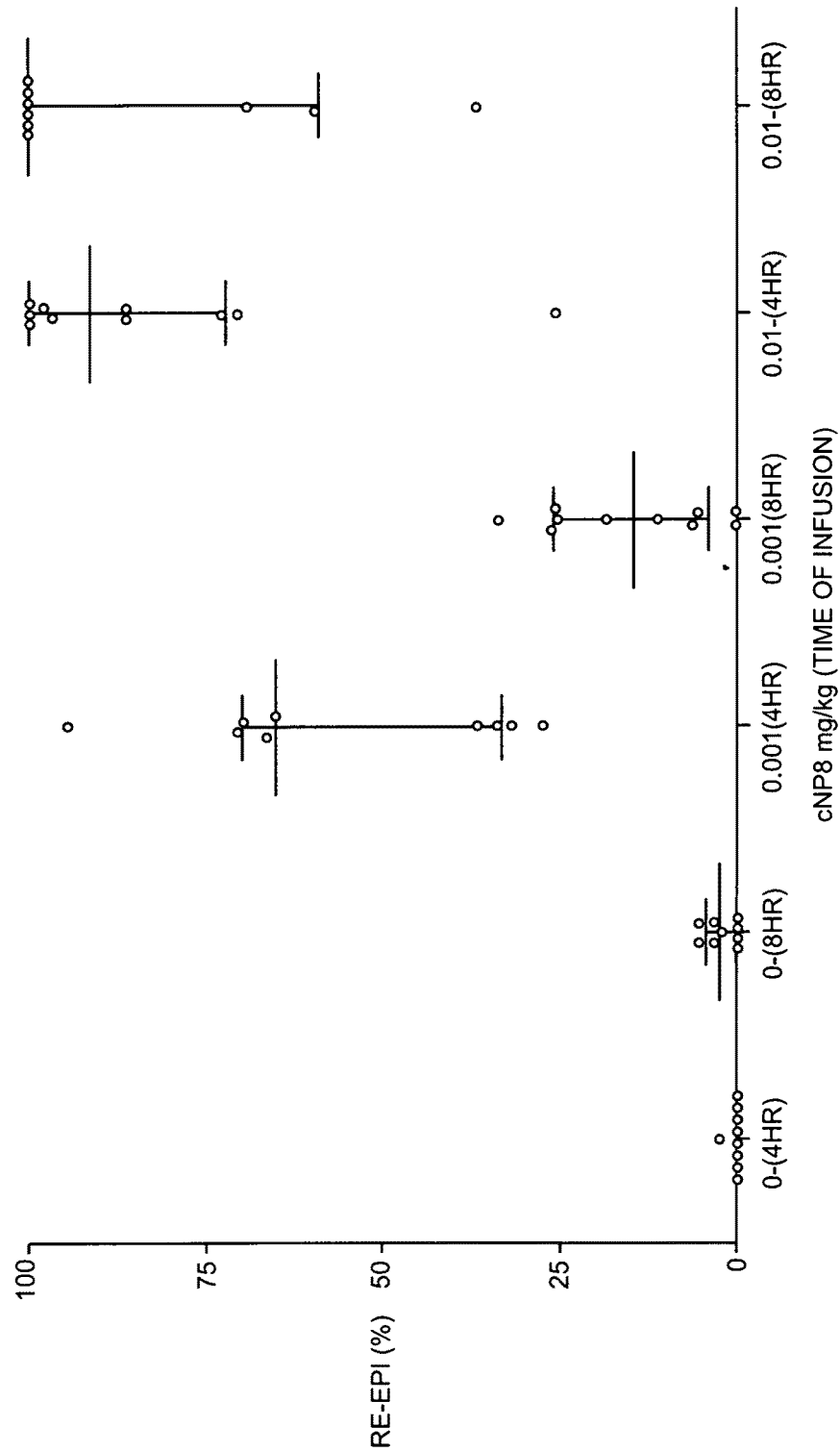
FIG. 8 shows the increase of re-epithelialization on day 14 at the wound site with intravenous cNP8 treatment in a porcine burn model.

Studies of I.V. Treatment of Porcine Burns with PDGF-BB and Formula I Peptide Formulations The vertical progression burn model (as shown in above topical experiment) was used to create burns on the backs of each of 4 pigs. Twenty burns (80° C./20 seconds) were made on the backs of each pig—one set of burns was made 8 hours prior to infusion, the second set was made 4 hours prior to infusion. Three pigs were treated with infusions of 0.001, 0.01 or 0.1 mg/kg of cNP8 and one pig was treated with an infusion of buffer, as control. Lyophilized cNP8 was reconstituted in PBS (11.6 mg/ml corrected-based on 75% pure) to get a 5 mM stock solution in the laboratory and filtered with a syringe filter with 0.22 um membrane. The concentration of filtered cNP8 solution was determined by reading OD280 and the concentration was calculated based on OD280=6.76 per mM cNP8. The cNP8 was diluted to 5 mM with PBS as necessary. The filtered cNP8 solution was aliquoted and stored at −80° C. Just before infusion, cNP8 was further diluted: a) 1:270 with PBS to get a 0.019 mM cNP8 solution. The injection amount was 3 ml/kg body weight of 0.019 mM cNP8 which is equal to 0.1 mg/kg body weight. b) 1:2700 with PBS to get a 0.0019 mM cNP8 solution. The injection was 3 ml/kg body weight of 0.0019 mM cNP8 which is equal to 0.01 mg/kg body weight. c) 1:27000 with PBS to get a 0.00019 mM cNP8 solution. The injection amount was 3 ml/kg body weight of 0.00019 mM cNP8 which is equal to 0.001 mg/kg body weight. The cNP8/buffer solution was intravenously administrated to each pig—4 hours or 8 hours after the burns are created on each pig. The room temperature infusion was administered via ear vein over a period of 30 minutes to the pig. General anesthesia was used during all procedures. Post injury biopsies were collected at various time points for histological analysis to determine percent re-epithelialization. As shown in FIGS. 7 and 8, re-epithelialization was markedly increased at 10 and 14 days post-injury with cNP8.

Pharmaceutical and Cosmetic Compositions

As an illustration of the invention, several cosmetic formulae will be cited. The formulae are representative of, but do not restrict, the invention:

Gel 1 g/100 g White soft paraffin 1.5 Cyclomethicone 6.0 Crodacol C90 0.5 Lubrajel MS10 Triethanolamine 0.3 Palmitoyl-HISKYILRWRPKNSV-OH (SEQ ID NO:10) 0.0005 Water, preservatives, fragrance q.s. 100 g The gel can be made by dissolving the peptide in the water at 80° C., mixing the first three components (paraffin, silicone and Crodacol) at 80° C., then blending the two phases, cool to 30° C., add the lubrajel, the preservatives and the fragrance. This gel may be used for daily application to the skin of the face, in particular around the eyes to reduce edematous infiltrations.

Cream 2 g/100 g Volpo S2 2.4 Volpo S20 2.6 Prostearyl 15 8.0 Beeswax 0.5 Stearoxydimethicone 3.0 Propylene glycol 3.0 Carbomer 0.25 Triethanolamine 0.25 Ceramide H03 (SEDERMA) 0.5 Acetyl-HIGKYGLRWRPKNSV-OH (SEQ ID NO:11) 0.001 Water, preservatives, fragrance q.s. 100 g This emulsion can be used to moisturize, restructure and soothe the facial skin, in particular on areas of fragile skin and to treat wrinkles. To produce the emulsion, one can dissolve ceramide HO3 in volpo 52, S20 and prostearyl 15 at 85° C., add beeswax and stearoxydimethicone; mix in the other ingredients in the water phase at 75-80° C., then blend the two phases, cool, and add fragrance. Ceramide HO3 is Tirhydroxypalmitamido myristyl ether.

Moisturizing and Anti-Wrinkle Foundation

Compound % (w/w) Demineralized water 53.36 10% KOH 1.30 Polysorbate 80 0.10 Titanium dioxide 6.00 Talc 3.05 Yellow iron oxide 1.80 Red iron oxide 1.00 Black iron oxide 0.15 Propylene glycol 6.00 Magnesium aluminum silicate 1.00 Sodium carboxymethylcellulose 0.12 DiPPG3 myristyl ether adipate 12.00 Isostearyl neopentanoate 4.00 Crodafos CS 20 4.00 Steareth-10 2.00 Cetyl alcohol 0.50 Steareth-2 0.50 Ceramide 2 (N-stearoyl-0.10 sphinganine) HIGKYGLRWRPKGSV-OH (SEQ ID NO:12) 0.0004 Preservatives q.s.

Subjects can be enrolled in a study on the use of a foundation cream as per above. The wrinkles around the eyes can be evaluated by self-evaluation/questionnaire and by the impression method. The product is applied to the target areas once daily for 56 days. The determinations are conducted on day 0 and day 56. As a control, the sites are treated with the same foundation cream devoid of peptide and are evaluated for improvement in the symptoms of cutaneous aging.

A number of embodiments of the invention have been described. Nevertheless, it will be understood that various modifications may be made without departing from the spirit and scope of the invention. Accordingly, other embodiments are within the scope of the following claims.

The invention claimed is:

1. A cyclized polypeptide consisting of Formula I:

$$\text{(I):} \quad H-X_1-X_2-K-Y-X_3-X_4-R-W-R-P-K-X_5-X_6-X_7 \quad \text{(SEQ ID NO: 1)}$$

wherein $X_1$ is I or G or L,
$X_2$ is S or G,
$X_3$ is I or G or L,
$X_4$ is L or G,
$X_5$ is N or G,
$X_6$ is absent or S, and
$X_7$ is absent or V; and
wherein no two consecutive amino acids in the first 13 amino acids of the polypeptide differ from the sequence HISKYILRWRPKN (SEQ NO:9),
wherein the polypeptide is not a linear or branched multimer of Formula I.

2. The cyclized polypeptide of claim 1, wherein the polypeptide is substituted with at least one of a lower acyl group at the N-terminus, a substituted or unsubstituted lower alkyl-, alkenyl-, alkynyl- or haloalkyl-amine group at the C-terminus and polyethylene glycol.

3. The cyclized polypeptide of claim 1, selected from the group consisting of HISKYILRWRPKNSV (SEQ ID NO:10), HIGKYGLRWRPKNSV (SEQ ID NO:11), HIGKYGLRWRPKGSV (SEQ ID NO:12), HGSKYGLRWRPKNSV (SEQ ID NO:13), HIGKYIGRWRPKNSV (SEQ ID NO:14), HGSKYIGRWRPKNSV (SEQ ID NO:15), and HGSKYIGRWRPKGSV (SEQ ID NO:16).

4. The cyclized polypeptide of claim 3, consisting of HIGKYGLRWRPKGSV (SEQ ID NO:12).

5. A composition comprising:
the cyclized polypeptide of claim 1, and;
a pharmaceutically acceptable excipient, carrier or diluent,
wherein the composition is suitable for a route of administration selected from injection, intravenous administration and topical administration to a patient.

6. The composition of claim 5, wherein the polypeptide is selected from the group consisting of HISKYILRWRPKNSV (SEQ ID NO:10), HIGKYGLRWRPKNSV (SEQ ID NO:11) HIGKYGLRWRPKGSV (SEQ ID NO:12), HGSKYGLRWRPKNSV (SEQ ID NO:13), HIGKYIGRWRPKNSV (SEQ ID NO:14), HGSKYIGRWRPKNSV (SEQ ID NO:15), and HGSKYIGRWRPKGSV (SEQ ID NO:16).

7. The composition of claim 6, wherein the polypeptide is HIGKYGLRWRPKGSV (SEQ ID NO:12).

8. A method of treating a patient with a wound selected from the group consisting of a surgical incision or extirpation, a traumatic injury, a thermal burn, a chemical burn, a lesion or ulceration of the patient's skin, mucosa, connective tissue, fascia, ligament, tendon, cartilage, nerve or muscle and a wound to the patient's bone, the method comprising:
administering to the patient a therapeutically effective amount of a composition comprising a cyclized polypeptide consisting of Formula I:

(I):
(SEQ ID NO: 1)
H-$X_1$-$X_2$-K-Y-$X_3$-$X_4$-R-W-R-P-K-$X_5$-$X_6$-$X_7$ wherein $X_1$ is I or G or L,
$X_2$ is S or G,
$X_3$ is I or G or L,
$X_4$ is L or G,
$X_5$ is N or G,
$X_6$ is absent or S, and
$X_7$ is absent or V; and
wherein no two consecutive amino acids in the first 13 amino acids of the polypeptide differ from the sequence HISKYILRWRPKN (SEQ ID NO:9),
wherein the polypeptide is not a linear or branched multimer of Formula I.

9. The method of claim 8, wherein the cyclized polypeptide is substituted with at least one of a lower acyl group at the N-terminus, a substituted or unsubstituted lower alkyl-, alkenyl-, alkynyl- or haloalkyl-amine group at the C-terminus and polyethylene glycol.

10. The method of claim 8, wherein the wound is a thermal burn or a chemical burn.

11. The method of claim 10, wherein the wound is a thermal burn.

12. The method of claim 8, wherein the cyclized polypeptide is selected from the group consisting of HISKYILRWRPKNSV (SEQ ID NO:10), HIGKYGLRWRPKNSV (SEQ ID NO:11), HIGKYGLRWRPKGSV (SEQ ID NO:12), HGSKYGLRWRPKNSV (SEQ ID NO:13), HIGKYIGRWRPKNSV (SEQ ID NO:14), HGSKYIGRWRPKNSV (SEQ ID NO:15), and HGSKYIGRWRPKGSV (SEQ ID NO:16).

13. The method of claim 8, wherein the cyclized polypeptide is HIGKYGLRWRPKGSV (SEQ ID NO:12).

* * * * *

UNITED STATES PATENT AND TRADEMARK OFFICE
CERTIFICATE OF CORRECTION

PATENT NO. : 11,548,935 B2
APPLICATION NO. : 16/341686
DATED : January 10, 2023
INVENTOR(S) : Clark et al.

It is certified that error appears in the above-identified patent and that said Letters Patent is hereby corrected as shown below:

In the Specification

Column 10, Line 8, SEQ ID NO: 90: Please correct "HGSKYIGRWRPKN" to read --HGSKYIGRWRPKNS--

Signed and Sealed this
Thirtieth Day of May, 2023

Katherine Kelly Vidal
*Director of the United States Patent and Trademark Office*